(12) United States Patent
Magurudeniya et al.

(10) Patent No.: US 12,371,855 B2
(45) Date of Patent: Jul. 29, 2025

(54) USE OF ENSILED BIOMASS FOR INCREASED EFFICIENCY OF THE PRETREATMENT OF BIOMASS

(71) Applicants: THE REGENTS OF THE UNIVERSITY OF CALIFORNIA, Oakland, CA (US); NATIONAL TECHNOLOGY AND ENGINEERING SOLUTIONS OF SANDIA, LLC, Albuquerque, NM (US)

(72) Inventors: Harsha D. Magurudeniya, Newport News, VA (US); Alberto Rodriguez, Oakland, CA (US); Nawa Raj Baral, Hayward, CA (US); Blake A. Simmons, San Francisco, CA (US); John M. Gladden, Alameda, CA (US)

(73) Assignees: THE REGENTS OF THE UNIVERSITY OF CALIFORNIA, Oakland, CA (US); NATIONAL TECHNOLOGY & ENGINEERING SOLUTIONS OF SANDIA, LLC, Albuquerque, NM (US)

( * ) Notice: Subject to any disclaimer, the term of this patent is extended or adjusted under 35 U.S.C. 154(b) by 203 days.

(21) Appl. No.: 17/242,256

(22) Filed: Apr. 27, 2021

(65) Prior Publication Data
US 2021/0332530 A1 Oct. 28, 2021

Related U.S. Application Data

(60) Provisional application No. 63/016,877, filed on Apr. 28, 2020.

(51) Int. Cl.
*D21C 3/20* (2006.01)
*C12N 1/20* (2006.01)
*D21C 11/00* (2006.01)
*C12R 1/40* (2006.01)

(52) U.S. Cl.
CPC .............. *D21C 3/20* (2013.01); *C12N 1/205* (2021.05); *D21C 11/0007* (2013.01); *C12R 2001/40* (2021.05)

(58) Field of Classification Search
CPC ........ D21C 3/20; D21C 11/0007; D21C 1/04; D21C 3/04; D21C 5/005; C12N 1/205; C12N 1/16; C12N 1/165; C12R 2001/40; C12R 2001/645
See application file for complete search history.

(56) References Cited

U.S. PATENT DOCUMENTS

| | | | |
|---|---|---|---|
| 6,177,575 B1 | 1/2001 | Arduengo, III et al. | |
| 7,985,567 B2 | 7/2011 | Chou et al. | |
| 8,420,833 B2 | 4/2013 | Katz et al. | |
| 8,852,902 B2 | 10/2014 | Katz et al. | |
| 9,109,175 B2 | 8/2015 | Lee et al. | |
| 9,200,298 B2 | 12/2015 | Lee et al. | |
| 9,322,042 B2 | 4/2016 | Sapra et al. | |
| 9,334,514 B2 | 5/2016 | Fortman et al. | |
| 9,376,691 B2 | 6/2016 | Peralta-Yahya et al. | |
| 9,376,728 B2 | 6/2016 | Zhang et al. | |
| 9,382,553 B2 | 7/2016 | Kirby et al. | |
| 9,624,482 B2 | 4/2017 | Sapra et al. | |
| 9,631,210 B2 | 4/2017 | Chou et al. | |
| 9,725,749 B2 | 8/2017 | Chen et al. | |
| 9,765,044 B2 | 9/2017 | Socha et al. | |
| 9,803,182 B2 | 10/2017 | Gladden et al. | |
| 9,862,982 B2 | 1/2018 | Zhang et al. | |
| 9,951,345 B2 | 4/2018 | Steen et al. | |
| 10,155,735 B2 | 12/2018 | Socha et al. | |
| 10,167,488 B2 | 1/2019 | Keasling et al. | |
| 2004/0097755 A1 | 5/2004 | Abbott et al. | |
| 2010/0196967 A1 | 8/2010 | Edye et al. | |
| 2020/0216863 A1 | 7/2020 | Xu et al. | |

FOREIGN PATENT DOCUMENTS

| | | |
|---|---|---|
| WO | 2009006386 A2 | 1/2009 |
| WO | 2009006429 A1 | 1/2009 |
| WO | 2009006430 A1 | 1/2009 |
| WO | 2009134899 A2 | 11/2009 |
| WO | 2010124266 A2 | 10/2010 |
| WO | 2010127318 A2 | 11/2010 |
| WO | 2012050931 A2 | 4/2012 |
| WO | 2012058686 A2 | 5/2012 |
| WO | 2012064740 A1 | 5/2012 |
| WO | 2012071439 A1 | 5/2012 |

(Continued)

OTHER PUBLICATIONS

Trulea, A., et al. "Ensiling sweet sorghum and maize stalks as feedstock for renewable energy production." Research Journal of Agricultural Science 45.3 (2013). (Year: 2013).*
Xu, Guo-Chao, et al. "Enhancing cellulose accessibility of corn stover by deep eutectic solvent pretreatment for butanol fermentation." Bioresource technology 203 (2016): 364-369. (Year: 2016).*
Rooke, John A. and Hatfield, Ronald D., "Biochemistry of Ensiling" (2003). Publications from USDA-ARS / UNL Faculty. 1399. (Year: 2003).*
Sun et al., "One-Pot Integrated Biofuel Production Using Low-Cost Biocompatible Protic Ionic Liquids." Green Chem. 19 (13), 3152-3163) (2017).
Greaves et al. "Protic Ionic Liquids: Properties and Applications" Chem. Rev. 108(1):206-237 (2008).

(Continued)

*Primary Examiner* — Kade Ariani
(74) *Attorney, Agent, or Firm* — Robin C. Chiang; LAWRENCE BERKELEY NATIONAL LABORATORY

(57) ABSTRACT

The present invention provides for a method to deconstruct a biomass: the method comprising: (a) ensiling a biomass to produce comprising one or more organic acids, and (b) introducing a solvent to the ensiled biomass to dissolve at least part of solid biomass in the solvent, wherein the solvent is an ionic liquid (IL) or deep eutectic solvent (DES), or mixture thereof, to form a solubilized biomass mixture.

11 Claims, 11 Drawing Sheets

(56) References Cited

FOREIGN PATENT DOCUMENTS

| | | |
|---|---|---|
| WO | 2012135389 A2 | 10/2012 |
| WO | 2012151214 A1 | 11/2012 |
| WO | 2014093402 A2 | 6/2014 |
| WO | 2015013674 A1 | 1/2015 |
| WO | 2016070125 A1 | 5/2016 |
| WO | 2016105538 A1 | 6/2016 |
| WO | 2017087982 A2 | 5/2017 |
| WO | 2017091781 A1 | 6/2017 |
| WO | 2017214159 A1 | 12/2017 |
| WO | 2017214332 A1 | 12/2017 |
| WO | 2018119152 A1 | 6/2018 |
| WO | 2018200888 A1 | 11/2018 |
| WO | 2018204424 A1 | 11/2018 |
| WO | 2019050990 A1 | 3/2019 |

OTHER PUBLICATIONS

Chen et al. "Distillable Ionic Liquids: reversible Amide O Alkylation", Angewandte Comm. 52:13392-13396 (2013).

King et al. "Distillable Acid-Base Conjugate Ionic Liquids for Cellulose Dissolution and Processing", Angewandte Comm. 50:6301-6305 (2011).

Vijayaraghavan et al. "CO2-based Alkyl Carbamate Ionic Liquids as Distillable Extraction Solvents", ACS Sustainable Chem. Engin. 2:31724-1728 (2014).

Idris et al. "Distillable Protic Ionic Liquids for Keratin Dissolution and Recovery", ACS Sustainable Chem. Engin. 2:1888-1894 (2014).

Huber et al., "Synergies between Bio- and Oil Refineries for the Production of Fuels from Biomass" Angew Chem Int Ed Engl, 46, 7184-7201 (2007).

Wyman et al., "Coordinated development of leading biomass pretreatment technologies" Bioresour. Technol., 96, 1959-1966 (2005).

Elgharbawy et al., "Ionic liquid pretreatment as emerging approaches for enhanced enzymatic hydrolysis of lignocellulosic biomass" Biochem. Eng. J., 2016, 109, 252-267 (2016).

Alonso et al., "Catalytic conversion of biomass to biofuels" Green Chem., 2010, 12, 1493 (2010).

Lynd et al., "Biocommodity Engineering" Biootechnol. Prog., 15, 777-793 (1999).

Wyman, Handbook on bioethanol: production and utilization, "Ethanol Production from Lignocellulosic Biomass: Overview", Routledge, pp. 1-18 (2018).

Kim, "Physico-Chemical Conversion of Lignocellulose: Inhibitor Effects and Detoxification Strategies: A Mini Review" Molecules, 2018, 23 (2018), 21 pages.

Linden et al., "Physico-Chemical Conversion of Lignocellulose: Inhibitor Effects and Detoxification Strategies: A Mini Review" Biotechnol. Bioeng., 30, 860-867 (1987).

Podkówka et al., "Chemical composition and quality of sweet sorghum and maize silages" J. Cent. Eur. Agric., 12, 294-303 (2011).

Stefaniak et al., "Variation in Biomass Composition Components among Forage, Biomass, Sorghum-Sudangrass, and Sweet Sorghum Types", Crop Sci., 52, 1949-1954 (2012).

Chen et al., "Ensiling Agricultural Residues for Bioethanol Production" Appl. Biochem. Biotechnol., 143, 80-92 (2007).

Oleskowicz-Popiel et al., "Ensiling e Wet-storage method for lignocellulosic biomassfor bioethanol production" Biomass and Bioenergy, 35, 2087-2092 (2011).

Ambye-Jensen et al., "Ensiling of wheat straw decreases the required temperature in hydrothermal pretreatment" Biotechnol. Biofuels, 6, 116 (2013).

Ambye-Jensen et al., "Combined ensiling and hydrothermal processing as efficient pretreatment of sugarcane bagasse for 2G bioethanol production" Biotechnol. Biofuels, 11, 336 (2018).

Kawahata et al., "Yeast genes involved in response to lactic acid and acetic acid: acidic conditions caused by the organic acids in *Saccharomyces cerevisiae* cultures induce expression of intracellular metal metabolism genes regulated by Aft1p" FEMS Yeast Res., 6, 924-936 (2006).

Ullah et al., "Quantitative Analysis of the Modes of Growth Inhibition by Weak Organic Acids in *Saccharomyces cerevisiae*", Appl. Environ. Microbiol., 78, 8377-8387 (2012).

Sundstrom et al., "Demonstrating a separation-free process coupling ionic liquid pretreatment, saccharification, and fermentation with Rhodosporidium toruloides to produce advanced biofuels", Green Chem., 20, 2870-2879 (2018).

Sun et al., "One-pot integrated biofuel production using low-cost biocompatible protic ionic liquids", Green Chem., 19, 3152-3163 (2017).

Rodriguez et al., "Conversion of depolymerized sugars and aromatics from engineered feedstocks by two oleaginous red yeasts" Bioresour. Technol., 86, 121365 (2019).

Mansfield et al., "Whole plant cell wall characterization using solution-state 2D NMR", Nat. Protoc., 7, 1579-1589 (2012).

Baral et al., "Techno-economic analysis and life-cycle greenhouse gas mitigation cost of five routes to bio-jet fuel blendstocks", Energy Environ. Sci., 12, 807-824 (2019).

Neupane et al., "Life-Cycle Greenhouse Gas and Water Intensity of Cellulosic Biofuel Production Using Cholinium Lysinate Ionic Liquid Pretreatment", Chem. Eng., 5, 10176-10185 (2017).

Baral et al., "Greenhouse Gas Footprint, Water-Intensity, and Production Cost of Bio-Based Isopentenol as a Renewable Transportation Fuel", ACS Sustain. Chem. Eng., 7, 15434-15444 (2019).

Baral et al., "Probabilistic Lifecycle Assessment of Butanol Production from Corn Stover Using Different Pretreatment Methods", Environ. Sci. Technol., 52, 14528-14537 (2018).

Xu et al., "Transforming biomass conversion with ionic liquids: process intensification and the development of a high-gravity, one-pot process for the production of cellulosic ethanol", Energy Environ. Sci., 9, 1042-1049 (2016).

Shi et al., "One-pot ionic liquid pretreatment and saccharification of switchgrass", Green Chem., 15, 2579-2589 (2013).

Xu et al., "Enzymatic hydrolysis and fermentability of corn stover pretreatedby lactic acid and/or acetic acid", J Biotechnol., 2009, 139, 300-305 (2009).

Johnson et al., "Natural acetylation impacts carbohydrate recovery during deconstruction of Populus trichocarpa wood", Biotechnol. Biofuels, 10, 48 (2017), 12 pages.

Sun et al., "Understanding pretreatment efficacy of four cholinium and imidazolium ionic liquids by chemistry and computation", Green Chem., 16, 2546-2557 (2014).

Papa et al., "Development of an integrated approach for a-pinene recovery and sugar production from loblolly pine using ionic liquids", Green Chem., 19, 1117-1127 (2017).

Masri et al.,"A sustainable, high-performance process for the economic production of waste-free microbial oils that can replace plant-based equivalents", Energy Environ. Sci. 12, 2717-2732 (2019).

\* cited by examiner

| Biomass | Dry sorghum (DS) % (w/w) | Ensiled sorghum (ES) % (w/w) |
|---|---|---|
| Glucan | 34 | 30 |
| Xylan | 18 | 15 |
| Lignin | 22 | 20 |
| Extractives | 18 | 26 |
| Ash | 4 | 7 |

USE OF ENSILED BIOMASS FOR INCREASED EFFICIENCY OF THE PRETREATMENT OF BIOMASS

CROSS-REFERENCE TO RELATED APPLICATIONS

This application claims priority to U.S. Provisional Patent Application Ser. No. 63/016,877, filed on Apr. 28, 2020, which is hereby incorporated by reference.

STATEMENT OF GOVERNMENTAL SUPPORT

The invention was made with government support under Contract Nos. DE-AC02-05CH11231 awarded by the U.S. Department of Energy. The government has certain rights in the invention.

FIELD OF THE INVENTION

The present invention is in the field of using ensiled biomass for biomass pretreatment.

BACKGROUND OF THE INVENTION

Pretreatment of lignocellulosic biomass is an essential step in any lignocellulosic conversion technology. Current pretreatment methods based on severe physio-chemical processes are effective. However, they are also costly and energy intensive. Biomass ensiling is a well-known method for generating an animal feed that preserves the green biomass and many of its nutrients (free sugars and proteins) through the anaerobic production of organic acids within the wet biomass by bacteria. Organic acids produced during the ensiling process are beneficial for both biomass preservation and to enhance digestibility.

Biofuels and bioproducts derived from sustainable feedstocks are considered a potential solution to address the challenges associated with human population growth. For efficient biofuel production, the biochemical conversion of lignocellulosic biomass has been frequently discussed in terms of process optimization as well as the reaction mechanism of various thermochemical processing (e.g., pretreatment) and biochemical conversion (e.g., enzymatic hydrolysis and fermentation). Current challenges to the realization of an affordable and scalable biomass conversion technology are those associated with complicated process designs, difficulties associated with efficient solvent recycle, and water consumption.

The development of efficient technologies for biomass deconstruction and conversion into high-value products has become increasingly important to facilitate the transition into a sustainable economy. Pretreatment is an essential step to achieve a high-yield conversion of the carbon stored in lignocellulosic biomass into biofuels and other products.[1-3] Common pretreatment methods require high temperature and pressure reaction conditions to effectively disrupt the structural integrity of biomass, which makes them costly and energy demanding.[7] In addition, high-severity pretreatment conditions could require extensive water washing prior to saccharification to reduce the concentration of enzymatic and microbial inhibitors that may be formed during the process.[8] Hence, the development of cheaper and more efficient pretreatment approaches remains a key challenge for lignocellulosic conversion technologies.

On the other hand, the year-round storage of wet biomass (moisture content of 60-75%) is a common practice to maintain an uninterrupted supply of animal feedstock. Wet biomass has several benefits relative to dry biomass, including lower risk of fire during storage, a wider harvest window, reduced soil or dirt contamination, and less material losses during the field operations.[9] However, improper storage of wet biomass may result in considerable degradation. Ensiling is a widely used method to store wet biomass by creating an anaerobic environment that is proven to preserve the quality of biomass for longer periods of time. Inoculated or naturally occurring bacteria produce organic acids in this environment, mainly lactic and acetic acids, which are not only beneficial for biomass preservation but also enhance its digestibility for cattle, sheep and other ruminants.[9-11] Considering that these organic acids are known to partially decompose cellulose, hemicellulose and lignin, the use of ensiled wet biomass could be advantageous for cellulosic biorefineries, specifically in processes that require large amounts of water. For example, one study evaluated the direct addition of glycosidase enzymes to several ensiled feedstocks including barley, triticale, wheat straw, cotton stalks, and triticale hay, and reported sugar yields of 40-45 wt %.[12] This suggests that ensiled biomass feedstocks require additional pretreatment to break up the complex lignocellulosic structure prior to enzymatic hydrolysis. Other studies have obtained higher glucose and xylose yields from ensiled biomass relative to dry biomass when enzymatic hydrolysis was coupled with a hot water pretreatment. Oleskowicz-Popiel et al. used hot water pretreatment at 190° C. for the ensiled grass mixtures of clover, maize, and rye and achieved glucose yields in the range of 55-60%, which are 15-20% higher than the direct saccharification.[13] Ensiling of wheat straw prior to performing a hot water pretreatment has also resulted in higher sugar yields relative to the unensiled biomass, however, these yields are still considered to be too low for cost-efficient ethanol production.[14,15]

In that regard, the high temperatures and long reaction times required for effective hydrothermal pretreatment could cause sugar degradation into byproducts, impacting the saccharification yields and producing microbial fermentation inhibitors such as furfural and hydroxymethylfurfural.[8] Although the organic acids in ensiled biomass could minimize degradation of hydrolyzed sugars to inhibitors when compared to inorganic acids (such as sulfuric acid), they may be toxic to organisms such as *Saccharomyces cerevisiae* and result in low ethanol yields.[16,17] The use of ionic liquids (ILs) as pretreatment agents has received increasing interest because of their ability to fractionate and deconstruct lignocellulosic biomass.[18] In particular, our group has developed a one-pot process that combines IL pretreatment using aqueous solutions of the IL cholinium lysinate [Ch][Lys] with enzymatic saccharification, without the need for washing or separating the biomass. This process has proven to be effective in solubilizing lignin and enabling the action of cellulase and hemicellulase enzymatic cocktails to release monomeric sugars at high titers and yields.[19,20] When coupled to a fermentation step, the majority of sugars and acids released by this treatment can be converted into biofuels and bioproducts by IL-tolerant organisms such as the oleaginous yeast *Rhodosporidium toruloides*.[19,21]

SUMMARY OF THE INVENTION

The present invention provides for a method to deconstruct a biomass: the method comprising: (a) ensiling a biomass to produce one or more organic acids, and (b) introducing a solvent to the ensiled biomass to dissolve at least part of solid biomass in the solvent, wherein the solvent is an ionic liquid (IL) or deep eutectic solvent (DES), or mixture thereof, to form a solubilized biomass mixture.

In some embodiments, the method further comprises (c) introducing an enzyme and/or a microbe to the solubilized biomass mixture such that the enzyme and/or microbe produces a sugar from the solubilized biomass mixture.

In some embodiments, the method further comprises (d) separating the sugar from the solubilized biomass mixture.

In some embodiments, steps (a), (b), (c) and/or (d) do not comprise or lack introducing or adding any water to the biomass or biomass mixture.

In some embodiments, the amount of sugar produced is equal to or more than the amount of sugar produced using an identical method except the identical method lacks the ensiling step (a) and the identical method using equal to or more than double, triple, or four times the amount of IL or DES used.

In some embodiments, the ensiling step (a) produces one or more toxic compounds in the ensiled biomass, and the microbe is resistant to the one or more toxic compounds.

In some embodiments, the one or more toxic compound is an organic acid, such as a straight chained or branched alkanoic acid (such as acetic acid, lactic acid, or formic acid), or an aromatic organic acid (such as benzoic acid, vanillic acid, or the like). In some embodiments, the organic acid has between about 2 to 10 carbon atoms.

In some embodiments, the microbe is *Rhodosporidium toruloides* or *Pseudomonas putida*.

In some embodiments, the DES is any combination of Lewis or Brønsted acid and base.

In some embodiments, the IL is a protic ionic liquid (PIL). In some embodiments, the protic ionic liquids (PILs) is formed with the combination of organic ammonium-based cations and organic carboxylic acid-based anions. PILs are acid-base conjugate TLs that can be synthesized via the direct addition of their acid and base precursors. Additionally, when sufficient energy is employed, they can dissociate back into their neutral acid and base precursors, while the PILs are re-formed upon cooling. This presents a suitable way to recover and recycle the ILs after their application. In some embodiments, the PIL (such as hydroxyethylammonium acetate-[Eth][OAc]) has already been demonstrated as an effective solvent for biomass pretreatment and is also relatively cheap due to its ease of synthesis (Sun, J.; Konda, N. V. S. N. M.; Parthasarathi, R.; Dutta, T.; Valiev, M.; Xu, F.; Simmons, B. A.; Singh, S. One-Pot Integrated Biofuel Production Using Low-Cost Biocompatible Protic Ionic Liquids. *Green Chem.* 2017, 19 (13), 3152-3163).

The present invention provides for compositions and methods described herein.

In some embodiments, the compositions and methods further comprise steps, features, and/or elements described in U.S. patent application Ser. No. 16/737,724, hereby incorporated by reference in its entirety.

In some embodiments, the method further comprises one or more of the following: (a) introducing the ensiled biomass and the IL or deep eutectic solvent (DES), or mixture thereof, into a vessel to form a one-pot composition, wherein the DES, or mixture thereof, solubilizes the biomass; (b) introducing an enzyme and/or a microbe to the one-pot composition such that the enzyme and/or microbe produce a biofuel and/or chemical compound from the solubilized biomass; and, (c) optionally separating the biofuel and/or chemical compound from the one-pot composition. In some embodiments, the introducing steps (a) and (b), and optionally the separating step (c), are continuous.

In some embodiments, the method, or one-pot method, does not require any solid-liquid separation step. In some embodiments, the one-pot method does not require adjustment of the pH level in the one-pot composition. In some embodiments, the one-pot method does not require any dilution, or addition of water or medium, after pretreatment and/or before saccharification and fermentation. In some embodiments, the reaction of the enzyme and the growth of the microbe occur in the same one-pot composition. In some embodiments, the IL, DES, or mixture thereof, is renewable as it can be continuous in use. In some embodiments, the one-pot method can produce a yield of sugar that is equal to or more than about 50%, 60%, 70%, 75%, or 80%, or any other value described herein.

In some embodiments, the one-pot biomass pretreatment, saccharification, and fermentation with bio-compatible deep eutectic solvents (DESs). The used bio-compatible DESs are tested for microbial, such as yeast, compatibility and toxicity. The pretreatment efficacy of the selected DESs are tested. The uses of the DESs for biomass processing eliminates the need to remove any solvent after biomass pretreatment, thus making the one-pot approach possible.

In some embodiments, using bio-compatible DESs enables a one-pot biomass conversion which eliminates the needs of mass transfer between reactors and the separation of solid and liquid. In some embodiments, the method does not require recycling any catalyst and/or enzyme. In some embodiments, the method requires less water usage than current biomass pretreatment. The method can produce fuels/chemicals at a higher titer and/or yield in a single vessel without any need for intermediate units of mass transfer and/or solid/liquid separation.

The advantages of the present invention are one or more of the following:
(1) reduces feedstock recalcitrance to enzymatic hydrolysis.
(2) reduces the amount of ILs required for effective pretreatment.
(3) provides a cheap route to synthesizing ILs by utilizing the endogenous organic acids.
(4) results in higher sugar conversion efficiencies.
(5) reduces MSP and GHG emissions.
(6) organic acids produced during ensiling can be used as an additional carbon source for bioconversion.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION OF THE INVENTION

Figure 1A:
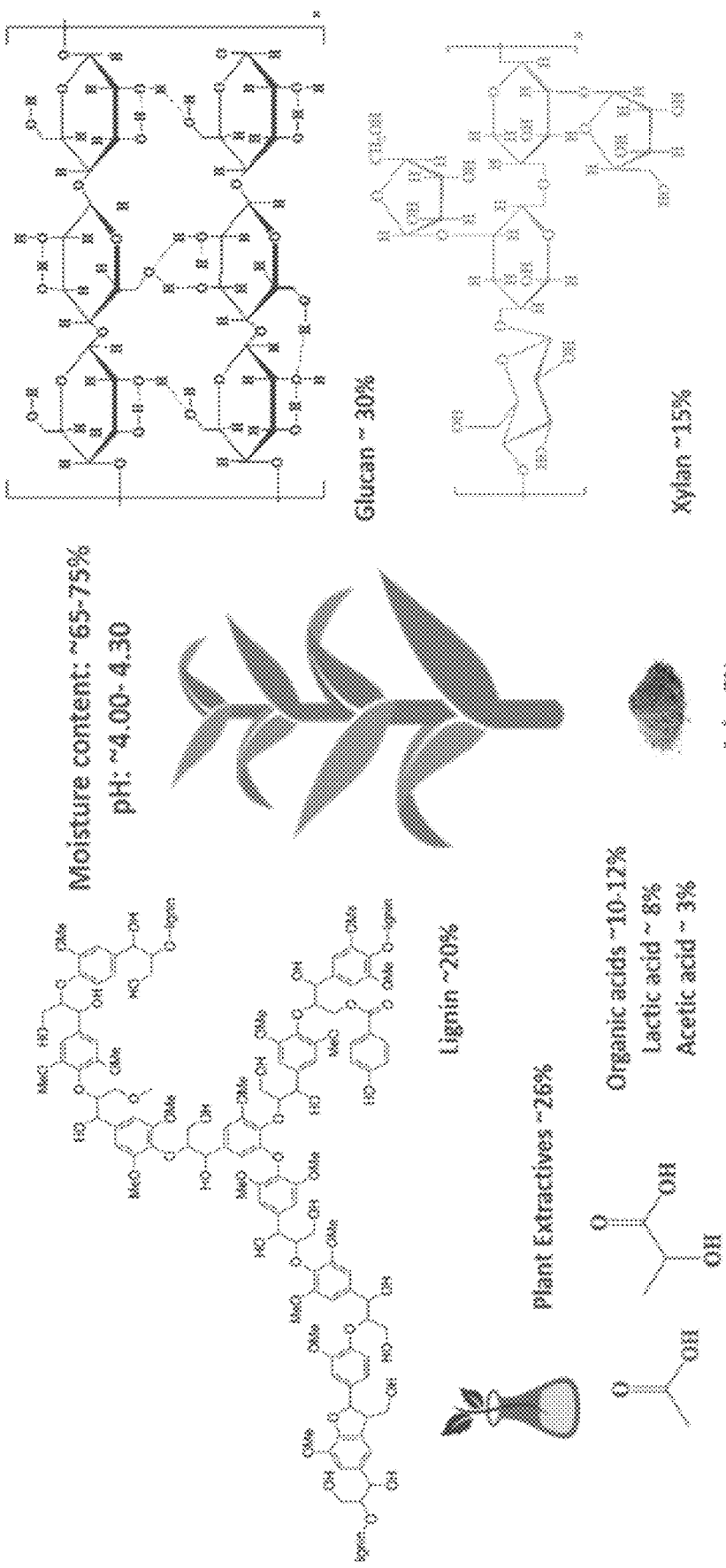
FIG. 1A. Structural composition of ensiled biomass sorghum.

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The term "about" when applied to a value, describes a value that includes up to 10% more than the value described, and up to 10% less than the value described.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Pretreatment of lignocellulosic biomass is an essential step in any lignocellulosic conversion technology. Current pretreatment methods based on severe physio-chemical processes are effective but are costly and energy intensive. Therefore, cheaper alternatives need to be developed. One approach is to identify methods of biomass processing in the field that condition the biomass and make it more easily deconstructed within a biorefinery. Biomass ensiling is a well-known method for generating animal feed that preserves the green biomass and many of its nutrients (free sugars and proteins) through the anaerobic production of organic acids within the wet biomass by bacteria. Organic acids produced during the ensiling process are beneficial for both biomass preservation and to enhance digestibility. The present invention is based on the insight that silage may also be more easily deconstructed in a lignocellulosic biorefinery. This invention demonstrates that the use of ensiled material enables a reduction in the severity of ionic liquid-based pretreatment through lower IL loadings (such as equal to or better than 2.5 wt % down from 10 wt %) and shorter saccharification times (1 day vs. 3 days).

Silage has been previously investigated as a lignocellulosic feedstock for bioconversion, but only hydrothermal/hot water pretreatment has been investigated. However, this pretreatment method results in low conversion efficiencies require higher temperatures and an extensive water washing prior to the enzymatic hydrolysis. Alternatively, many ionic liquids (ILs) have been shown to be effective at biomass pretreatment. For example, cholinium lysinate (ChLys) in 90% water, has been demonstrated to be effective for biomass pretreatment in a one-pot configuration owing to its effectiveness in solubilizing lignin.

The present invention demonstrates that the amount of ChLys can be reduced up to 4-fold when pretreating an ensiled biomass, such as ensiled sorghum, resulting in high sugar yields. In addition to reducing IL loading, it is shown the biomass is more rapidly enzymatically saccharified relative to non-ensiled biomass, such as ensiled sorghum, with the reaction almost complete in about 24 hours. In addition, at lower ChLys loadings, less acid may be required to adjust the pH to about 5 for saccharification. In some embodiments, under certain conditions, the pH does not need adjusting, thus eliminating the use of acid in a one-pot process.

Preliminary results confirm that the ensiled biomass, such as ensiled sorghum, yields higher sugar conversions (about 10-15%) comparable to the respective dry biomass sorghum pretreatments. Enzymatic saccharification of the pretreated silage sorghum at about 140° C., releases about ≥90% to ≥85% of the maximum theoretical glucose at the IL-loadings of about 5% to 2.5%, respectively. Also, the pretreated silage sorghum at about 95° C., released about ≥80% of the maximum theoretical glucose for both IL-loadings of about 5% to 2.5%.

According to the techno-economic analysis, the selling price of ethanol at the IL-loading rate of 2.5% is reduced by 13% relative to the ethanol price at IL-loading rate of 5%. Also, the greenhouse gas emissions (GHG) at the IL-loading rate of 2.5% is reduced by 60% relative to the GHG emissions from ethanol at IL-loading rate of 5%. Overall, the use of ensiled biomass enables a reduction in IL use and reduces the saccharification time.

Ionic Liquid

Ionic liquids (ILs) are salts that are liquids rather than crystals at room temperatures. It will be readily apparent to those of skill that numerous ILs can be used in the present invention. In some embodiments of the invention, the IL is suitable for pretreatment of the biomass and for the hydrolysis of cellulose by thermostable cellulase. Suitable ILs are taught in ChemFiles (2006) 6(9) (which are commercially available from Sigma-Aldrich, Milwaukee, Wis.). Such suitable ILs include, but are not limited to, 1-alkyl-3-alkylimidazolium alkanate, 1-alkyl-3-alkylimidazolium alkylsulfate, 1-alkyl-3-alkylimidazolium methylsulfonate, 1-alkyl-3-alkylimidazolium hydrogensulfate, 1-alkyl-3-alkylimidazolium thiocyanate, and 1-alkyl-3-alkylimidazolium halide, wherein an "alkyl" is an alkyl group comprising from 1 to 10 carbon atoms, and an "alkanate" is an alkanate comprising from 1 to 10 carbon atoms. In some embodiments, the "alkyl" is an alkyl group comprising from 1 to 4 carbon atoms. In some embodiments, the "alkyl" is a methyl group, ethyl group or butyl group. In some embodiments, the "alkanate" is an alkanate comprising from 1 to 4 carbon atoms. In some embodiments, the "alkanate" is an acetate. In some embodiments, the halide is chloride.

In some embodiments, the IL includes, but is not limited to, 1-ethyl-3-methylimidazolium acetate (EMIN Acetate), 1-ethyl-3-methylimidazolium chloride (EMIN Cl), 1-ethyl-3-methylimidazolium hydrogensulfate (EMIM $HOSO_3$), 1-ethyl-3-methylimidazolium methylsulfate (EMIM $MeOSO_3$), 1-ethyl-3-methylimidazolium ethylsulfate (EMIM $EtOSO_3$), 1-ethyl-3-methylimidazolium methanesulfonate (EMIM $MeSO_3$), 1-ethyl-3-methylimidazolium tetrachloroaluminate (EMIM $AlCl_4$), 1-ethyl-3-methylimidazolium thiocyanate (EMIM SCN), 1-butyl-3-methylimidazolium acetate (BMTM Acetate), 1-butyl-3-methylimidazolium chloride (BMIM Cl), 1-butyl-3-methylimidazolium hydrogensulfate (BMIM $HOSO_3$), 1-butyl-3-methylimidazolium methanesulfonate (BMIM $MeSO_3$), 1-butyl-3-methylimidazolium methylsulfate (BMIM $MeOSO_3$), 1-butyl-3-methylimidazolium tetrachloroaluminate (BMTM AlCl4), 1-butyl-3-methylimidazolium thiocyanate (BMTM SCN), 1-ethyl-2,3-dimethylimidazolium ethylsulfate (EDIM $EtOSO_3$), Tris(2-hydroxyethyl)methylammonium methylsulfate (MTEOA $MeOSO_3$), 1-methylimidazolium chloride (MIM Cl), 1-methylimidazolium hydrogensulfate (MIM $HOSO_3$), 1,2,4-trimethylpyrazolium methylsulfate, tributylmethylammonium methylsulfate, choline acetate, choline salicylate, and the like.

In some embodiments, the ionic liquid is a chloride ionic liquid. In other embodiments, the ionic liquid is an imidazolium salt. In still other embodiments, the ionic liquid is a 1-alkyl-3-imidazolium chloride, such as 1-ethyl-3-methylimidazolium chloride or 1-butyl-3-methylimidazolium chloride.

In some embodiments, the ionic liquids used in the invention are pyridinium salts, pyridazinium salts, pyrimidium salts, pyrazinium salts, imidazolium salts, pyrazolium salts, oxazolium salts, 1,2,3-triazolium salts, 1,2,4-triazolium salts, thiazolium salts, isoquinolium salts, quinolinium salts isoquinolinium salts, piperidinium salts and pyrrolidinium salts. Exemplary anions of the ionic liquid include, but are not limited to halogens (e.g., chloride, fluoride, bromide and iodide), pseudohalogens (e.g., azide and isocyanate), alkyl carboxylate, sulfonate, acetate and alkyl phosphate.

Additional ILs suitable for use in the present invention are described in U.S. Pat. Nos. 6,177,575; 9,765,044; and, 10,155,735; U.S. Patent Application Publication Nos. 2004/0097755 and 2010/0196967; and, PCT International Patent Application Nos. PCT/US2015/058472, PCT/US2016/063694, PCT/US2017/067737, and PCT/US2017/036438 (all of which are incorporated in their entireties by reference). It will be appreciated by those of skill in the art that others ILs that will be useful in the process of the present invention are currently being developed or will be developed in the future, and the present invention contemplates their future use. The ionic liquid can comprise one or a mixture of the compounds.

In some embodiments, the IL is a protic ionic liquid (PIL). Suitable protic ionic liquids (PILs) include fused salts with a melting point less than 100° C. with salts that have higher melting points referred to as molten salts. Suitable PPILs are disclosed in Greaves et al. "Protic Ionic Liquids: Properties and Applications" *Chem. Rev.* 108(1):206-237 (2008). PILs can be prepared by the neutralization reaction of certain Brønsted acids and Brønsted bases (generally from primary, secondary or tertiary amines, which are alkaline) and the fundamental feature of these kinds of ILs is that their cations have at least one available proton to form hydrogen bond with anions. In some embodiments, the protic ionic liquids (PILs) are formed from the combination of organic ammonium-based cations and organic carboxylic acid-based anions. PILs are acid-base conjugate ILs that can be synthesized via the direct addition of their acid and base precursors. In some embodiments, the PIL is a hydroxyalkylammonium carboxylate. In some embodiments, the hydroxyalkylammonium comprises a straight or branched C1, C2, C3, C4, C5, C6, C7, C8, C9, or C10 chain. In some embodiments, the carboxylate comprises a straight or branched C1, C2, C3, C4, C5, C6, C7, C8, C9, or C10 chain. In some embodiments, the carboxylate is substituted with one or more hydroxyl groups. In some embodiments, the PIL is a hydroxyethylammonium acetate.

In some embodiments, the protic ionic liquid (PIL) is disclosed by U.S. Patent Application Publication No. 2004/0097755, hereby incorporated by reference.

Suitable salts for the method include combinations of organic ammonium-based cations (such as ammonium, hydroxyalkylammonium, or dimethylalkylammonium) with organic carboxylic acid-based anions (such as acetic acid derivatives (C1-C8), lactic acid, glycolic acid, and DESs such as ammonium acetate/lactic acid).

Suitable IL, such as distillable IL, are disclosed in Chen et al. "Distillable Ionic Liquids: reversible Amide O Alkylation", *Angewandte Comm.* 52:13392-13396 (2013), King et al. "Distillable Acid-Base Conjugate Ionic Liquids for Cellulose Dissolution and Processing", *Angewandte Comm.* 50:6301-6305 (2011), and Vijayaraghavan et al. "$CO_2$-based Alkyl Carbamate Ionic Liquids as Distillable Extraction Solvents", *ACS Sustainable Chem. Engin.* 2:31724-1728 (2014), all of which are hereby incorporated by reference.

Suitable PIL, such as distillable PIL, are disclosed in Idris et al. "Distillable Protic Ionic Liquids for Keratin Dissolution and Recovery", *ACS Sustainable Chem. Engin.* 2:1888-1894 (2014) and Sun et al. "One-pot integrated biofuel production using low-cost biocompatible protic ionic liquids", *Green Chem.* 19(13):3152-3163 (2017), all of which are hereby incorporated by reference.

In some embodiments, the PILs are formed with the combination of organic ammonium-based cations and organic carboxylic acid-based anions. PILs are acid-base conjugate ILs that can be synthesized via the direct addition of their acid and base precursors. Additionally, when sufficient energy is employed, they can dissociate back into their neutral acid and base precursors, while the PILs are re-formed upon cooling. This presents a suitable way to recover and recycle the ILs after their application. In some embodiments, the PIL (such as hydroxyethylammonium acetate-[Eth][OAc]) is an effective solvent for biomass pretreatment and is also relatively cheap due to its ease of synthesis (Sun et al., *Green Chem.* 19(13):3152-3163 (2017)).

Deep Eutectic Solvent (DES)

DESs are systems formed from a eutectic mixture of Lewis or Brønsted acids and bases which can contain a variety of anionic and/or cationic species. DESs can form a eutectic point in a two-component phase system. DESs are formed by complexation of quaternary ammonium salts (such as, choline chloride) with hydrogen bond donors (HBD) such as amines, amides, alcohols, or carboxylic acids. The interaction of the HBD with the quaternary salt reduces the anion-cation electrostatic force, thus decreasing the melting point of the mixture. DESs share many features of conventional ionic liquid (IL), and promising applications would be in biomass processing, electrochemistry, and the like. Any Lewis or Brønsted acid and base combination can be used in the invention as long as the combination is distillable.

In some embodiments, DES is prepared using an alcohol (such as glycerol or ethylene glycol), amines (such as urea), and an acid (such as oxalic acid or lactic acid). The present invention can use renewable DESs with lignin-derived phenols as HBDs. Both phenolic monomers and phenol mixture readily form DES upon heating at 100° C. with specific molar ratio with choline chloride. This class of DES does not require a multistep synthesis. The novel DES is synthesized from lignin which is a renewable source.

Both monomeric phenols and phenol mixture can be used to prepare DES. DES is capable of dissolving biomass or lignin, and can be utilized in biomass pretreatment and other applications. Using DES produced from biomass could lower the cost of biomass processing and enable greener routes for a variety of industrially relevant processes.

The DES, or mixture thereof, is bio-compatible: meaning the DES, or mixture thereof, does not reduce or does not significantly reduce the enzymatic activity of the enzyme, and/or is not toxic, and/or does not reduce or significantly reduce, the growth of the microbe. A "significant" reduction is a reduction to 70, 80, 90, or 95% or less of the enzyme's enzymatic activity and/or the microbe's growth (or doubling time), if the DES, or mixture thereof, was not present.

In some embodiments, the DES, or mixture thereof, comprises a quaternary ammonium salt and/or glycerol. In some embodiments, the DES, or mixture thereof, comprises a quaternary ammonium salt and/or glycerol. In some embodiments, the quaternary ammonium salt and/or glycerol have a molar ratio of about 1:1 to about 1:3. In some embodiments, the quaternary ammonium salt and/or glycerol have a molar ratio of about 1:1.5 to about 1:2.5. In some embodiments, the quaternary ammonium salt and/or glycerol have a molar ratio of about 1:1.8 or 1:1.9 to about 1:2.1 or 1:2.2. In some embodiments, the quaternary ammonium salt and/or glycerol have a molar ratio of about 1:2. In some embodiments, the quaternary ammonium salt is a choline halide, such choline chloride.

In some embodiments, the DES is distillable if the DABCS or DES can be recovered at least equal to or more than about 50%, 55%, 60%, 65%, 70%, 75%, 80%, or 85% yield by distilling over vacuum at a temperature at about 100° C., 110° C., 120° C., 130° C., 140° C., 150° C., or 160° C., or any temperature between any two of the preceding temperatures. In some embodiments, the method results in the releasing of at least equal to or more than about 60%, 65%, 70%, 75%, 80%, or 85% fermentable sugars.

In some embodiments, the DES can be one taught in WO 2018/204424 (Seema Singh et al.), which is hereby incorporated in its entirety by reference.

In some embodiments, the method further comprises heating the one-pot composition, optionally also comprising the enzyme and/or microbe, to a temperature that is equal to, about, or near the optimum temperature for the enzymatic activity of the enzyme and/or growth of the microbe. In some embodiments, the enzyme is a genetically modified host cell capable of converting the cellulose in the biomass into a sugar. In some embodiments, there is a plurality of enzymes. In some embodiments, the microbe is a genetically modified host cell capable of converting a sugar produced from the biomass into a biofuel and/or chemical compound. In some embodiments, there is a plurality of microbes. In some embodiments, the introducing steps (a) and (b) together produce a sugar and a lignin from the biomass. The lignin can further be processed to produce a DES. The sugar is used for growth by the microbe.

In some embodiments, the solubilizing is full, near full (such as at least about 70, 80, or 90%), or partial (such as at least about 10, 20, 30, 40, 50, or 60%). In some embodiments, the one-pot composition is a slurry. When the steps (a) to (c), and optionally step (d) are continuous, the one-pot composition is in a steady state.

In some embodiments, all or some of the one-pot composition is further pretreated as follows: the method further comprising: optionally separating the sugar and the lignin in the one-pot composition, depolymerizing and/or converting the lignin into one or more lignin derived monomeric phenol, or a mixture thereof, providing the one or more lignin derived monomeric phenol, or a mixture thereof, in a solution, introducing one or more quaternary ammonium salts, or a mixture thereof, to the solution, heating the solution, such that the preceding two steps together result in the synthesis of a DES, optionally forming a DES system from the DES synthesized in the heating step, and optionally repeating the preceding steps using the DES system formed in forming a DES system step in the introducing step (a).

In some embodiments, the heating step comprises increasing the temperature of the solution to a value within a range of about 75° C. to about 125° C. In some embodiments, the heating step (h) comprises increasing the temperature of the solution to a value within a range of about 80° C. to about 120° C. In some embodiments, the heating step comprises increasing the temperature of the solution to a value within a range of about 90° C. to about 110° C. In some embodiments, the heating step comprises increasing the temperature of the solution to about 100° C.

Deep eutectic solvents (DESs) share the promising solvent properties of ionic liquids. They show low volatility, wide liquid range, water-compatibility, non-flammability, non-toxicity, biocompatibility and biodegradability. Furthermore, DES can be easily prepared from readily available materials at high purities and low cost compared to ILs. Lignin is the second most abundant naturally occurring polymer next to cellulose, which represents a significant component of carbon on earth. Large amounts of technical lignins such as Kraft lignin and lignosulfonate are produced as by-products in the pulp and paper industries. It is also expected that more lignin will become available in coming years as the production capability of second generation of biofuels increases. As a renewable and resource, lignin and lignin derived products (phenolic) are an important material. DESs with lignin-derived phenolic compounds either as a single monomer or phenolic mixture can be used in the present invention.

The one-pot biomass pretreatment, saccharification, and fermentation with bio-compatible deep eutectic solvents (DESs). The used bio-compatible DESs are tested for microbial, such as yeast, compatibility and toxicity. The pretreatment efficacy of the selected DESs are tested. The uses of the DESs for biomass processing eliminates the need to remove any solvent after biomass pretreatment, thus making the one-pot approach possible.

In some embodiments, using bio-compatible DESs enables a one-pot biomass conversion which eliminates the needs of mass transfer between reactors and the separation of solid and liquid. In some embodiments, the method does not require recycling any catalyst and/or enzyme. In some embodiments, the method requires less water usage than current biomass pretreatment. The method can produce fuels/chemicals at a higher titer and/or yield in a single vessel without any need for intermediate units of mass transfer and/or solid/liquid separation. In some embodiments, the vessel is made of a material that is inert, such as stainless steel or glass, that does not react or interfere with the reactions in the one-pot composition.

Enzyme

In some embodiments, the enzyme is a cellulase. In some embodiments, the enzyme is thermophilic or hyperthermophilic. In some embodiments, the enzyme is any enzyme taught in U.S. Pat. Nos. 9,322,042; 9,376,728; 9,624,482; 9,725,749; 9,803,182; and 9,862,982; and PCT International Patent Application Nos. PCT/US2015/000320, PCT/US2016/063198, PCT/US2017/036438, PCT/US2010/032320, and PCT/US2012/036007 (all of which are incorporated in their entireties by reference).

Microbe

In some embodiments, the microbe is any prokaryotic or eukaryotic cell, with any genetic modifications, taught in U.S. Pat. Nos. 7,985,567; 8,420,833; 8,852,902; 9,109,175; 9,200,298; 9,334,514; 9,376,691; 9,382,553; 9,631,210; 9,951,345; and 10,167,488; and PCT International Patent Application Nos. PCT/US14/48293, PCT/US2018/049609, PCT/US2017/036168, PCT/US2018/029668, PCT/US2008/068833, PCT/US2008/068756, PCT/US2008/068831, PCT/US2009/042132, PCT/US2010/033299, PCT/US2011/053787, PCT/US2011/058660, PCT/US2011/059784, PCT/US2011/061900, PCT/US2012/031025, and PCT/US2013/074214 (all of which are incorporated in their entireties by reference).

Generally, although not necessarily, the microbe is a yeast or a bacterium. In some embodiments, the microbe is *Rhodosporidium toruloides* or *Pseudomonas putida*. In some embodiments, the microbe is a Gram negative bacterium. In some embodiments, the microbe is of the phylum Proteobactera. In some embodiments, the microbe is of the class Gammaproteobacteria. In some embodiments, the microbe is of the order Enterobacteriales. In some embodiments, the microbe is of the family Enterobacteriaceae. Examples of suitable bacteria include, without limitation, those species assigned to the *Escherichia, Enterobacter, Azotobacter, Erwinia, Bacillus, Pseudomonas, Klebsielia, Proteus, Salmonella, Serratia, Shigella, Rhizobia, Vitreoscilla*, and *Paracoccus* taxonomical classes. Suitable eukaryotic microbes include, but are not limited to, fungal cells. Suitable fungal cells are yeast cells, such as yeast cells of the *Saccharomyces* genus.

Yeasts suitable for the invention include, but are not limited to, *Yarrowia, Candida, Bebaromyces, Saccharomyces, Schizosaccharomyces* and *Pichia* cells. In some embodiments, the yeast is *Saccharomyces cerevisae*. In some embodiments, the yeast is a species of *Candida*, including but not limited to *C. tropicalis, C. maltosa, C. apicola, C. paratropicalis, C. albicans, C. cloacae, C. guillermondii, C. intermedia, C. lipolytica, C. panapsilosis* and *C. zeylenoides*. In some embodiments, the yeast is *Candida tropicalis*. In some embodiments, the yeast is a non-oleaginous yeast. In some embodiments, the non-oleaginous yeast is a *Saccharomyces* species. In some embodiments, the *Saccharomyces* species is *Saccharomyces cerevisiae*. In some embodiments, the yeast is an oleaginous yeast. In some embodiments, the oleaginous yeast is a *Rhodosporidium* species. In some embodiments, the *Rhodosporidium* species is *Rhodosporidium toruloides*.

In some embodiments the microbe is a bacterium. Bacterial host cells suitable for the invention include, but are not limited to, *Escherichia, Corynebacterium, Pseudomonas, Streptomyces*, and *Bacillus*. In some embodiments, the *Escherichia* cell is an *E. coli, E. albertii, E. fergusonii, E. hermanii, E. marmotae*, or *E. vulneris*. In some embodiments, the *Corynebacterium* cell is *Corynebacterium glutamicum, Corynebacterium kroppenstedtii, Corynebacterium alimapuense, Corynebacterium amycolatum, Corynebacterium diphtheriae, Corynebacterium efficiens, Corynebacterium jeikeium, Corynebacterium macginleyi, Corynebacterium matruchotii, Corynebacterium minutissimum, Corynebacterium renale, Corynebacterium striatum, Corynebacterium ulcerans, Corynebacterium urealyticum*, or *Corynebacterium uropygiale*. In some embodiments, the *Pseudomonas* cell is a *P. putida, P. aeruginosa, P. chlororaphis, P. fluorescens, P. pertucinogena, P. stutzeri, P. syringae, P. cremoricolorata, P. entomophila, P. fulva, P. monteilii, P. mosselii, P. oryzihabitans, P. parafluva*, or *P. plecoglossicida*. In some embodiments, the *Streptomyces* cell is a *S. coelicolor, S. lividans, S. venezuelae, S. ambofaciens, S. avermitilis, S. albus*, or *S. scabies*. In some embodiments, the *Bacillus* cell is a *B. subtilis, B. megaterium, B. lichenformis, B. anthracis, B. amyloliquefaciens*, or *B. pumilus*.

Biofuel

In some embodiments, the biofuel produced is ethanol, or any other organic molecule, described produced in a cell taught in U.S. Pat. Nos. 7,985,567; 8,420,833; 8,852,902; 9,109,175; 9,200,298; 9,334,514; 9,376,691; 9,382,553; 9,631,210; 9,951,345; and 10,167,488; and PCT International Patent Application Nos. PCT/US14/48293, PCT/US2018/049609, PCT/US2017/036168, PCT/US2018/029668, PCT/US2008/068833, PCT/US2008/068756, PCT/US2008/068831, PCT/US2009/042132, PCT/US2010/033299, PCT/US2011/053787, PCT/US2011/058660, PCT/US2011/059784, PCT/US2011/061900, PCT/US2012/

031025, and PCT/US2013/074214 (all of which are incorporated in their entireties by reference).

Biomass

The biomass comprising the lignin can be any biomass disclosed herein. The biomass can be obtained from one or more feedstock, such as softwood feedstock, hardwood feedstock, grass feedstock, and/or agricultural feedstock, or a mixture thereof. In some embodiments, the biomass is a lignocellulosic biomass comprising cellulose, hemicellulose, and lignin in various ratios (depending on the biomass source). The cellulose, hemicellulose, and lignin are held together by covalent and strong hydrogen bonds forming a complex matrix recalcitrant to facile depolymerization. The biomass can also be from any post-production or post-consumer source that comprises lignin and/or lignosulfonate, such as used coffee grounds, spent pulping liquids (red or brown liquor) from sulfite pulping, or a wastestream.

Softwood feedstocks include, but are not limited to, *Araucaria* (e.g. *A. cunninghamii, A. angustifolia, A. araucana*); softwood Cedar (e.g. *Juniperus virginiana, Thuja plicata, Thuja occidentalis, Chamaecyparis thyoides Callitropsis nootkatensis*); Cypress (e.g. *Chamaecyparis, Cupressus Taxodium, Cupressus arizonica, Taxodium distichum, Chamaecyparis obtusa, Chamaecyparis lawsoniana, Cupressus sempervirens*); Rocky Mountain Douglas fir; European Yew; Fir (e.g. *Abies balsamea, Abies alba, Abies procera, Abies amabilis*); Hemlock (e.g. *Tsuga canadensis, Tsuga mertensiana, Tsuga heterophylla*); Kauri; Kaya; Larch (e.g. *Larix decidua, Larix kaempferi, Larix laricina, Larix occidentalis*); Pine (e.g. *Pinus nigra, Pinus banksiana, Pinus contorta, Pinus radiata, Pinus ponderosa, Pinus resinosa, Pinus sylvestris, Pinus strobus, Pinus monticola, Pinus lambertiana, Pinus taeda, Pinus palustris, Pinus rigida, Pinus echinata*); Redwood; Rimu; Spruce (e.g. *Picea abies, Picea mariana, Picea rubens, Picea sitchensis, Picea glauca*); Sugi; and combinations/hybrids thereof.

For example, softwood feedstocks which may be used herein include cedar; fir; pine; spruce; and combinations thereof. The softwood feedstocks for the present invention may be selected from loblolly pine (*Pinus taeda*), radiata pine, jack pine, spruce (e.g., white, interior, black), Douglas fir, *Pinus silvestris, Picea abies*, and combinations/hybrids thereof. The softwood feedstocks for the present invention may be selected from pine (e.g. *Pinus radiata, Pinus taeda*); spruce; and combinations/hybrids thereof.

Hardwood feedstocks include, but are not limited to, *Acacia*; *Afzelia*; *Synsepalum duloificum*; *Albizia*; Alder (e.g. *Alnus glutinosa, Alnus rubra*); Applewood; Arbutus; Ash (e.g. *F. nigra, F. quadrangulata, F. excelsior, F. pennsylvanica lanceolata, F. latifolia, F. profunda, F. americana*); Aspen (e.g. *P. grandidentata, P. tremula, P. tremuloides*); Australian Red Cedar (*Toona ciliata*); Ayna (*Distemonanthus benthamianus*); Balsa (*Ochroma pyramidale*); Basswood (e.g. *T. americana, T. heterophylla*); Beech (e.g. *F. sylvatica, F. grandifolia*); Birch; (e.g. *Betula populifolia, B. nigra, B. papyrifera, B. lenta, B. alleghaniensis/B. lutea, B. pendula, B. pubescens*); Blackbean; Blackwood; Bocote; Boxelder; Boxwood; Brazilwood; Bubing a; Buckeye (e.g. *Aesculus hippocastanum, Aesculus glabra, Aesculus flava/Aesculus octandra*); Butternut; *Catalpa*; Chemy (e.g. *Prunus serotina, Prunus pennsylvanica, Prunus avium*); Crabwood; Chestnut; Coachwood; Cocobolo; Corkwood; Cottonwood (e.g. *Populus balsamifera, Populus deltoides, Populus sargentii, Populus heterophylla*); Cucumbertree; Dogwood (e.g. *Cornus florida, Cornus nuttallii*); Ebony (e.g. *Diospyros kurzii, Diospyros melanida, Diospyros crassiflora*); Elm (e.g. *Ulmus americana, Ulmus procera, Ulmus thomasii, Ulmus rubra, Ulmus glabra*); *Eucalyptus*; Greenheart; Grenadilla; Gum (e.g. *Nyssa sylvatica, Eucalyptus globulus, Liquidambar styraciflua, Nyssa aquatica*); Hickory (e.g. *Carya alba, Carya glabra, Carya ovata, Carya laciniosa*); Hornbeam; Hophornbeam; Ipê; Iroko; Ironwood (e.g. *Bangkirai, Carpinus caroliniana, Casuarina equisetifolia, Choricbangarpia subargentea, Copaifera* spp., *Eusideroxylon zwageri, Guajacum officinale, Guajacum sanctum, Hopea odorata, Ipe, Krugiodendronferreum, Lyonothamnus lyonii* (*L. floribundus*), *Mesua ferrea, Olea* spp., *Olneya tesota, Ostrya virginiana, Parrotia persica, Tabebuia serratifolia*); Jacarandi; Jotoba; Lacewood; Laurel; Limba; *Lignum vitae*; Locust (e.g. *Robinia pseudacacia, Gleditsia triacanthos*); Mahogany; Maple (e.g. *Acer saccharum, Acer nigrum, Acer negundo, Acer rubrum, Acer saccharinum, Acer pseudoplatanus*); Meranti; Mpingo; Oak (e.g. *Quercus macrocarpa, Quercus alba, Quercus stellata, Quercus bicolor, Quercus virginiana, Quercus michauxii, Quercus prinus, Quercus muhlenbergii, Quercus chrysolepis, Quercus lyrata, Quercus robur, Quercus petraea, Quercus rubra, Quercus velutina, Quercus laurifolia, Quercus falcata, Quercus nigra, Quercus phellos, Quercus texana*); Obeche; Okoume; Oregon Myrtle; California Bay Laurel; Pear; Poplar (e.g. *P. balsamifera, P. nigra,* Hybrid Poplar (*Populus×canadensis*)); Ramin; Red cedar; Rosewood; Sal; Sandalwood; *Sassafras*; Satinwood; Silky Oak; Silver Wattle; Snakewood; Sourwood; Spanish cedar; American sycamore; Teak; Walnut (e.g. *Juglans nigra, Juglans regia*); Willow (e.g. *Salix nigra, Salix alba*); Yellow poplar (*Liriodendron tulipifera*); Bamboo; Palmwood; and combinations/hybrids thereof.

For example, hardwood feedstocks for the present invention may be selected from *Acacia*, Aspen, Beech, *Eucalyptus*, Maple, Birch, Gum, Oak, Poplar, and combinations/hybrids thereof. The hardwood feedstocks for the present invention may be selected from *Populus* spp. (e.g. *Populus tremuloides*), *Eucalyptus* spp. (e.g. *Eucalyptus globulus*), *Acacia* spp. (e.g. *Acacia dealbata*), and combinations thereof.

Grass feedstocks include, but are not limited to, $C_4$ or $C_3$ grasses, e.g. Switchgrass, Indiangrass, Big Bluestem, Little Bluestem, Canada Wildrye, Virginia Wildrye, and Goldenrod wildflowers, etc, amongst other species known in the art.

Agricultural feedstocks include, but are not limited to, agricultural byproducts such as husks, stovers, foliage, and the like. Such agricultural byproducts can be derived from crops for human consumption, animal consumption, or other non-consumption purposes. Such crops can be corps such as corn, wheat, sorghum, rice, soybeans, hay, potatoes, cotton, or sugarcane. The feedstock can arise from the harvesting of crops from the following practices: intercropping, mixed intercropping, row cropping, relay cropping, and the like.

In some embodiment, the biomass is ensiled by placing the biomass in an enclosed container or room, such as a silo, or by piling it in a heap covered by an airproof layer, such as a plastic film. The biomass undergoing the ensiling, known as the silage, goes through a bacterial fermentation process resulting in production of volatile fatty acids. In some embodiment, the ensiling comprises adding ensiling agents such as sugars, lactic acid or inculants. In some embodiments, the ensiled biomass comprises one or more toxic compounds. In some embodiments, when ensiled biomass comprises one or more toxic compounds, the microbe is resistant to the one or more toxic compounds.

References cited herein (which are all individually and specifically incorporated by reference):

1. J. Holm and U. Lassi, in *Ionic liquids: applications and perspectives*, ed. A. Kokorin, InTech, 2011.
2. G. W. Huber and A. Corma, *Angew Chem Int Ed Engl*, 2007, 46, 7184-7201.
3. C. E. Wyman, B. E. Dale, R. T. Elander, M. Holtzapple, M. R. Ladisch, and Y. Y. Lee, *Bioresour. Technol.*, 2005, 96, 1959-1966.
4. A. A. Elgharbawy, M. Z. Alam, M. Moniruzzaman, and M. Goto, *Biochem. Eng. J.*, 2016, 109, 252-267.
5. D. M. Alonso, J. Q. Bond, and J. A. Dumesic, *Green Chem.*, 2010, 12, 1493.
6. L. R. Lynd, C. E. Wyman, and T. U. Gerngross, *Biotechnol. Prog.*, 1999, 15, 777-793.
7. C. E. Wyman, in *Handbook on bioethanol: production and utilization*, Routledge, 2018, pp. 1-18.
8. D. Kim, *Molecules*, 2018, 23.
9. J. C. Linden, L. L. Henk, V. G. Murphy, D. H. Smith, B. C. Gabrielsen, R. P. Tengerdy, and L. Czako, *Biotechnol. Bioeng.*, 1987, 30, 860-867.
10. Z. Podkówka and L. Podkówka, j. cent. eur. agric., 2011, 12, 294-303.
11. T. R. Stefaniak, J. A. Dahlberg, B. W. Bean, N. Dighe, E. J. Wolfrum, and W. L. Rooney, *Crop Sci.*, 2012, 52, 1949.
12. Y. Chen, R. R. Sharma-Shivappa, and C. Chen, *Appl. Biochem. Biotechnol.*, 2007, 143, 80-92.
13. P. Oleskowicz-Popiel, A. B. Thomsen, and J. E. Schmidt, *Biomass and Bioenergy*, 2011, 35, 2087-2092.
14. M. Ambye-Jensen, S. T. Thomsen, Z. Kádár, and A. S. Meyer, *Biotechnol. Biofuels*, 2013, 6, 116.
15. M. Ambye-Jensen, R. Balzarotti, S. T. Thomsen, C. Fonseca, and Z. Kádár, *Biotechnol. Biofuels*, 2018, 11, 336.
16. M. Kawahata, K. Masaki, T. Fujii, and H. Iefuji, *FEMS Yeast Res.*, 2006, 6, 924-936.
17. A. Ullah, R. Orij, S. Brul, and G. J. Smits, *Appl. Environ. Microbiol.*, 2012, 78, 8377-8387.
18. V. Ward and L. Rehmann, in *Handbook of biorefinery research and technology*, ed. J. M. Park, Springer Netherlands, Dordrecht, 2018, pp. 1-21.
19. E. Sundstrom, J. Yaegashi, J. Yan, F. Masson, G. Papa, A. Rodriguez, M. Mirsiaghi, L. Liang, Q. He, D. Tanjore, T. R. Pray, S. Singh, B. Simmons, N. Sun, J. Magnuson, and J. Gladden, *Green Chem.*, 2018, 20, 2870-2879.
20. J. Sun, N. V. S. N. Konda, R. Parthasarathi, T. Dutta, M. Valiev, F. Xu, B. A. Simmons, and S. Singh, *Green Chem.*, 2017, 19, 3152-3163.
21. A. Rodriguez, N. Ersig, G. M. Geiselman, K. Seibel, B. A. Simmons, J. K. Magnuson, A. Eudes, and J. M. Gladden, *Bioresour. Technol.*, 2019, 286, 121365.
22. S. D. Mansfield, H. Kim, F. Lu, and J. Ralph, *Nat. Protoc.*, 2012, 7, 1579-1589.
23. A. Sluiter, B. Hames, R. Ruiz, C. Scarlata, J. Sluiter, D. Templeton, and D. Crocker, *Laboratory Analytical Procedure (LAP)*, 2012.
24. N. R. Baral, O. Kavvada, D. Mendez-Perez, A. Mukhopadhyay, T. S. Lee, B. A. Simmons, and C. D. Scown, *Energy Environ. Sci.*, 2019, 12, 807-824.
25. B. Neupane, N. V. S. N. Konda, S. Singh, B. A. Simmons, and C. D. Scown, *ACS Sustain. Chem. Eng.*, 2017, 5, 10176-10185.
26. D. Humbird, R. Davis, L. Tao, C. Kinchin, D. Hsu, A. Aden, P. Schoen, J. Lukas, B. Olthof, M. Worley, D. Sexton, and D. Dudgeon, *Process Design and Economics for Biochemical Conversion of Lignocellulosic Biomass to Ethanol: Dilute-Acid Pretreatment and Enzymatic Hydrolysis of Corn Stover*, National Renewable Energy Laboratory (NREL), Golden, CO (United States), 2011.
27. N. R. Baral, O. Kavvada, D. Mendez-Perez, A. Mukhopadhyay, T. S. Lee, B. Simmons, and C. D. Scown, *ACS Sustain. Chem. Eng.*, 2019.
28. N. R. Baral, C. Quiroz-Arita, and T. H. Bradley, *Environ. Sci. Technol.*, 2018, 52, 14528-14537.
29. F. Xu, J. Sun, N. V. S. N. M. Konda, J. Shi, T. Dutta, C. D. Scown, B. A. Simmons, and S. Singh, *Energy Environ. Sci.*, 2016, 9, 1042-1049.
30. J. Shi, J. M. Gladden, N. Sathitsuksanoh, P. Kambam, L. Sandoval, D. Mitra, S. Zhang, A. George, S. W. Singer, B. A. Simmons, and S. Singh, *Green Chem.*, 2013, 15, 2579.
31. J. Xu, M. H. Thomsen, and A. B. Thomsen, *J Biotechnol.*, 2009, 139, 300-305.
32. A. M. Johnson, H. Kim, J. Ralph, and S. D. Mansfield, *Biotechnol. Biofuels*, 2017, 10, 48.
33. N. Sun, R. Parthasarathi, A. M. Socha, J. Shi, S. Zhang, V. Stavila, K. L. Sale, B. A. Simmons, and S. Singh, *Green Chem.*, 2014, 16, 2546-2557.
34. G. Papa, J. Kirby, N. V. S. N. Murthy Konda, K. Tran, S. Singh, J. D. Keasling, G. F. Peter, and B. A. Simmons, *Green Chem.*, 2017, 19, 1117-1127.
35. M. Masri, D. Garbe, N. Mehlmer, and T. Brück, *Energy Environ. Sci.*, 2019.

Example 1

Ensiled Biomass Increases Ionic Liquid Pretreatment Efficiency and Reduces Biofuel Production Cost and Carbon Footprint Pretreatment is an essential step to enable the efficient conversion of lignocellulosic biomass to biofuels and bioproducts. The most effective pretreatment methods currently in use are based on severe thermochemical approaches, which are costly and energy-intensive. Here the common method of ensiling grassy biomass can be used as a preprocessing step to increase the conversion efficiency under milder pretreatment conditions is explored. The impact of replacing dry biomass with ensiled biomass on the deconstruction efficiency, process economics, and carbon footprint of a lignocellulosic biorefinery that employs a separation-free ionic liquid pretreatment coupled to enzymatic saccharification and microbial conversion is determined. Our results indicate that the use of ensiled biomass allows for a reduction in both the amount of ionic liquid (from 5 to 2.5 wt %) and the time required for enzymatic saccharification (from 72 h to 24 h) without sacrificing efficiency. It is shown that the resulting hydrolysate can be used to cultivate an engineered strain of *Rhodosporidium toruloides* to convert >90% of the monomeric sugars and acetic, lactic and benzoic acids released from the biomass into the biofuel precursor bisabolene. Overall, it is estimated that the replacement of field-dried biomass sorghum with ensiled sorghum in combination with an ionic liquid-based deconstruction process can reduce the minimum selling price and carbon footprint of biofuel production in a biorefinery by at least 13.4% and 8.2%, respectively.

In this study, the hypothesis that the combination of both biomass preprocessing through ensiling and one-pot pretreatment can increase biomass deconstruction efficiency without reducing hydrolysate compatibility for downstream biological conversion is tested. In particular, this study focuses on the effects of variable IL loadings, pH values for saccharification, and enzyme loading and reaction time. The biocompatibility of the generated hydrolysates is confirmed by cultivating an engineered *R. toruloides* strain that produces the sesquiterpene bisabolene. Lastly, we performed a techno economic analysis and life cycle assessment to evaluate the impact of this new process on the overall cost and environmental footprint.

2. Materials and Methods

2.1. Chemicals and Feedstock

Ensiled and dry biomass sorghum are kindly provided by the laboratory of Daniel Putnam at the University of California, Davis and Jeff Dhalberg at Kearney agricultural research and extension center. Ensiled sorghum samples are stored at 22° C. in a sealed plastic bag before use in all experiments. Commercial enzyme cocktails Cellic® CTec 3 and HTec 3 are generously provided by Novozymes (Davis, CA). Choline hydroxide (46% in $H_2O$) is purchased from Sigma-Aldrich (St. Louis, MO), L-lysine monohydrate is purchased from VWR and hydrochloric acid (36-37.5%) is purchased from J. T. Baker (Phillipsburg, NJ) and used without further purification.

2.2. Compositional Analysis

Deionized water is added to ensiled sorghum biomass at a ratio of 10:1 (w/v), i.e., 1 g of sample to 10 mL of water and sonicated for 2-3 h. The pH of storage extracts is determined using a pH meter (Mettler-Toledo International Inc, Columbus, OH). The collected extracts are filtered using 0.45 m PTFE filters and analyzed using HPLC to characterize and quantify organic acids, as described below. Five different potential acids (lactic, acetic, butyric, propionic and formic) are tracked during the analysis. The moisture content of the ensiled sorghum biomass is measured gravimetrically after freeze-drying in a lyophilizer. All the soluble compounds such as organic acids, proteins, sugar degradation products and other extractives are removed using deionized water, ethanol and acetone according to literature precedents.[22] Compositional analysis of extracted ensiled sorghum biomass is performed according to NREL acidolysis protocols (LAP).[23] Briefly, 300 mg of biomass and 3 mL of 72% $H_2SO_4$ are incubated at 30° C. while shaking at 300 rpm for 1 h. The solution is diluted to 4% $H_2SO_4$ with 84 mL of deionized water and autoclaved for 1 h at 121° C. The reaction is quenched by placing samples into an ice bath and samples from the liquid fraction are collected for quantification of sugar monomers before removing the biomass by filtration. Acid soluble lignin is estimated by measuring the UV absorption of the acid hydrolysis supernatant at 240 nm using a UV-Vis spectrophotometer (Nanodrop 2000, Thermo Scientific, USA). Acid insoluble lignin is quantified gravimetrically from the solid after heating overnight at 105° C. (to obtain the weight of acid-insoluble lignin+ash) and then at 575° C. for at least 6 h (corresponding to the weight of ash).

2.3. Synthesis of the IL [Ch][Lys]

Lysine monohydrate (0.4 mol, 65.68 g) is weighed into a 500 mL round bottom flask and dissolved in 100 mL deionized water at room temperature to obtain a clear solution (light lime-yellow). Then the flask is mounted on an ice-bath (3-5° C.) and $N_2$ is purged for 20-30 mins. Next 46 wt % of choline hydroxide in water (0.4 mol, 105.15 g) is added dropwise to lysine solution while maintaining the temperature of the ice-bath (3-5° C.). The mixture is stirred for 48 h at room temperature. Excess water is removed under reduced pressure and the mixture is added to acetonitrile/methanol (9:1, v/v) to remove the excess starting materials. Finally, the solvents are removed under reduced pressure and the mixture is freeze-dried to get the final product (yield ~95%, light orange). The obtained product is characterized by neat NMR using DMSO-$d_6$ as an external lock solvent.

2.4. One-Pot Ionic Liquid Pretreatment

The reactions comprised in the one-pot ionic liquid pretreatment are performed according to previously published methods[19,29,30] with the following modifications: the ensiled sorghum biomass (20 wt % solids loading) is mixed with [Ch][Lys] loadings of 10 wt %, 5 wt %, and 2.5 wt % in 60 mL capped pressure vials. All the pretreatment experiments are carried out in an oil bath at 140° C. and 95° C. for 3 h. The same experimental conditions are used for dry sorghum biomass as a control. Scaled-up pretreatment experiments for both ensiled and dry sorghum are carried out using a 1 L 4520 Parr benchtop reactor (Parr Instrument Company, Moline, IL, USA) equipped with three arms and a self-centering anchor with PTFE wiper blades.

2.5. Enzymatic Hydrolysis

After pretreatment, the pH of the resulting slurry is adjusted to pH 5 with 10 M hydrochloric acid. Commercial enzyme cocktails containing cellulase (Cellic® CTec3) and hemicellulase (Cellic® HTec3) mixed at a 9:1 (v/v) ratio are then directly added at an enzyme loading of 10 mg enzyme product per one gram of starting biomass. Three glass beads are added to each vial to facilitate mixing during enzymatic hydrolysis. Enzymatic hydrolysis is conducted at 50° C. for 72 h, with constant agitation on an Enviro Genie SI-1200 rotator platform (Scientific Industries, Inc., Bohemia, NY).

2.6. Analytical Methods

Monomeric sugars and organic acids are quantified with an Agilent Technologies 1200 series HPLC system equipped with an Aminex HPX-87H column (BioRad Laboratories, USA), kept at 60° C. during analysis. 4 mM sulfuric acid is used as a mobile phase with a flow rate of 0.6 mL/min. Prior to analysis, samples are filtered through 0.45 μm nylon centrifuge filters and 5 μL sample injection volumes are used. The compounds of interest are monitored using a refractive index detector and their concentrations are calculated by comparison of peak areas to standard curves made with pure compounds. To quantify lignin-derived monomeric aromatics, the same instrument equipped with an Eclipse Plus Phenyl-hexyl column (250 mm length, 4.6 mm diameter, 5 μm particle size; Agilent Technologies, USA) is used. This column is kept at 50° C. during the analysis. The mobile phase is composed of 10 mM ammonium acetate in water (solvent A) and 10 mM ammonium acetate in acetonitrile 90% (solvent B), prepared from a stock solution of 100 mM ammonium acetate and 0.7% formic acid in water. The following mobile phase gradient profile is used: 30% B (0 min; 0.5 mL/min), 80% B (12 min; 0.5 mL/min), 100% B (12.1 min; 0.5 mL/min), 100% B (12.6 min; 1 mL/min), 30% B (12.8 min; 1 mL/min), 30% B (15.6 min; 1 mL/min). Metabolites are quantified with calibration curves made with authentic standard compounds.

To measure the amount of bisabolene produced in the cultivations (see section 2.7), the dodecane overlays at the end of the experiments are collected and diluted in pure dodecane spiked with 40 mg/L of pentadecane, to be used as an internal standard. The samples are then analyzed by GC-MS using an Agilent Technologies 6890N system, equipped with a 5973 mass selective detector and a DB-5 ms column (30 m×250 μm×0.25 μm, Agilent Technologies, USA). Splitless 1 μl injections are used on a GC oven program consisting of 100° C. for 0.75 min, followed by a ramp of 20° C. per min until 300° C., and held 1 min at 300° C. Injector and MS quadrupole detector temperatures are 250° C. and 150° C., respectively. The bisabolene concentrations reported here correspond to the actual concentrations in the dodecane layer, calculated by integration of the peak area values obtained in selective ion monitoring mode and compared to the areas obtained from a calibration curve made with pure bisabolene.

2.7. Microbial Cultivations

The yeast strain used in this work is deposited in the Joint BioEnergy Institute public registry and can be accessed at the webpage for //public-registry.jbei.org (ID number in parentheses): *Rhodosporidium toruloides* GB2.0 (JBx_086452). To perform fermentations, seed cultures are generated by inoculating the organism in 5 mL of YPD broth and incubating overnight at 30° C. and 200 rpm. Overnight cultures are diluted 10 times with fresh YPD media and grown until mid-exponential phase prior to transferring to the cultivation media. Before inoculation, ammonium sulfate is added to clarified hydrolysates obtained from the one-pot process at a final concentration of 2 g/L. A 1:9 v/v ratio of $NH_4SO_4$:hydrolysate is used to prepare hydrolysates at 90% final concentration and a 1:5:4 ratio v/v of $NH_4SO_4$:hydrolysate:water is used to prepare hydrolysates at 50% final concentration. For bisabolene production experiments, the initial pH of the media is adjusted to 7.5 using concentrated NaOH or $H_2SO_4$, filtered through 0.45 μm nylon centrifuge filters (VWR, USA), and transferred to 48-well FlowerPlates (m2p labs, Germany) employing 780 μL of media, 20 μL of cells and 200 μL of a dodecane overlay, and covered with sterile AeraSeal films (Excel Scientific, USA). The plates are incubated for 7 days in a humidity-controlled incubator with orbital shaking at 900 rpm. The entire contents of each well are collected in eppendorf tubes, where the dodecane layer, supernatant, and cells are separated by centrifugation and each fraction is kept frozen until analysis. The cell pellets are then resuspended in 800 μL of water, diluted forty-fold with water, and 100 μL are transferred to 96-well plates to measure final optical density at 600 nm using a SpectraMax Plus 384 reader (Molecular Devices, USA). All cultivations are performed in triplicate. The percentile substrate utilization is calculated as the difference in concentration of glucose, xylose, acetic or benzoic acids at the beginning and end of the fermentation.

2.8. Technoeconomic Analysis and Life-Cycle Assessment

The impact of shifting from dry sorghum to an ensiled sorghum feedstock on costs and greenhouse gas (GHG) emissions is evaluated in the context of downstream ethanol production as a representative process. For the dry and ensiled sorghum scenarios, a biorefinery sized to process 2000 dry metric tons of biomass per day is modeled. The minimum ethanol selling price and associated life-cycle GHG emissions to identify key cost and carbon footprint drivers associated with the biomass deconstruction stage is calculated. The minimum selling price of bisabolene based on the first proof of concept of bisabolene production in *R. toruloides* demonstrated in this study is further determined. Bisabolane is a potential jet fuel blendstock, which can be produced via catalytic hydrogenation of bisabolene.[24] The process models developed in SuperPro Designer are consistent with prior technoeconomic models of lignocellulosic biomass to ethanol[25,26] and bisabolene[24] production processes. The biomass feedstock supply and handling as well as deconstruction stages are modified in this study. These are briefly discussed in the following paragraphs. The capital and operating parameters for other stages of the entire biofuel production chain are consistent with prior studies.[24,26]

The dry biomass supply system includes biomass sorghum production, windrowing, sun drying at the field, baling, stacking, transportation from the field to the biorefinery (includes loading and unloading at each end), and storage next to the biorefinery under the tarp. The moisture content of biomass at the time of harvest is assumed to be 60%, which requires about 7 days of solar drying in the field to reach the expected moisture content of biomass sorghum bales of 20%. On the other hand, the ensiled biomass sorghum feedstock supply system does not require drying in the field. Biomass is harvested in the form of chopped biomass by using the forage harvester, directly loaded on the truck, transported to the biorefinery (includes unloading), and ensiled next to the biorefinery in a bunker silo. The detailed input parameters considered for these two different biomass supply routes are documented in Table 3. The methods used to determine biomass feedstock supply cost and associated GHG emissions are consistent with a recent biomass sorghum feedstock supply model developed at JBEI/LBNL.[27]

TABLE 3

Primary nutrients for biomass sorghum and their prices (The same parameters are used for dry and ensiled biomass supply system systems.

| Parameter | Unit | μ | a | b | σ | Probability distribution |
|---|---|---|---|---|---|---|
| Nitrogen[1-5] | kg/ha | 121.24 | 48.00 | 217.00 | 51.88 | Triangular |
| Phosphorus[1,3,5] | kg/ha | 23.89 | 9.30 | 67.25 | 16.74 | Triangular |
| Potassium[1,3,5] | kg/ha | 168.09 | 20.00 | 293.66 | 100.53 | Triangular |
| Price of nitrogen[6-10] | $/kg | 1.06 | 0.60 | 1.40 | 0.34 | Triangular |
| Price of phosphorus[6-10] | $/kg | 1.01 | 0.82 | 1.20 | 0.15 | Triangular |
| Price of potassium[6-10] | $/kg | 1.09 | 0.91 | 1.26 | 0.14 | Triangular |
| Herbicides[11-13] | kg/ha | 3.13 | 1.79 | 5.60 | — | Triangular |
| Herbicides[11-14] | $/ha | 62.12 | 24.46 | 111.20 | — | Triangular |

Note:

μ = average value;

a = minimum value;

b = maximum value;

σ = standard deviation

Biomass feedstock handling at the biorefinery includes conveying, size reduction (only for bale or dry biomass supply system), and short-term storage. The size reduction step is not considered for the ensiled biomass as the particle size of the chopped biomass is assumed to be in the range of 0.12 to 1.9 cm, which can be directly fed to the pretreatment reactor. The biomass deconstruction stage, including pretreatment and enzymatic hydrolysis, is modified based on the methods and operating conditions considered for the experimental analysis as discussed earlier. The process equipment data are gathered from similar prior studies.[25,28] Following the rigorous material and energy balances for each unit operation, capital and operating costs as well as material and energy requirements for each stage of the entire biofuel production chain are determined. The economic evaluation parameters and the methods used to determine carbon footprint are documented in Table 4.

TABLE 4

Operating data and purchasing price for forage harvester (for the ensiled biomass supply system).

| Forage harvester | Unit | μ | a | b | σ | Probability distribution |
|---|---|---|---|---|---|---|
| Productivity[15-17] | t/h | 31.67 | 26.33 | 49.22 | 10.45 | TRI |
| Field efficiency[15,16,18] | % | 76.43 | 60.00 | 90.00 | 9.88 | TRI |
| Fuel consumption[16] | L/h | 61.61 | 28.62 | 104.15 | 26.85 | TRI |
| Labor rate[19] | $/h | 19.36 | 12.62 | 29.81 | 6.82 | TRI |
| Wagon unloading time[15,16] | h | 0.03 | 0.02 | 0.05 | 0.02 | TRI |
| Purchasing price[15,16,20-22] | $/unit | 230,570 | 179,334 | 259,725 | 30,710 | TRI |
| Repair and maintenance[15,16,18] | % | 7.36 | 5.57 | 10.14 | — | TRI |
| Service life[15,16,18] | yr | 4.50 | 4.00 | 5.00 | — | Constant |
| Salvage value[15,16,18] | % | 18.60 | 15.00 | 25.00 | — | Constant |
| Material loss[15,17] | % | 6.00 | 2.00 | 10.00 | — | TRI |

Note:
μ = average value,
a = minimum value;
b = maximum value;
σ = standard deviation

3. Results and Discussion

3.1. Compositional Analysis of Dry and Ensiled Biomass Sorghum

Figures 1B, 2:
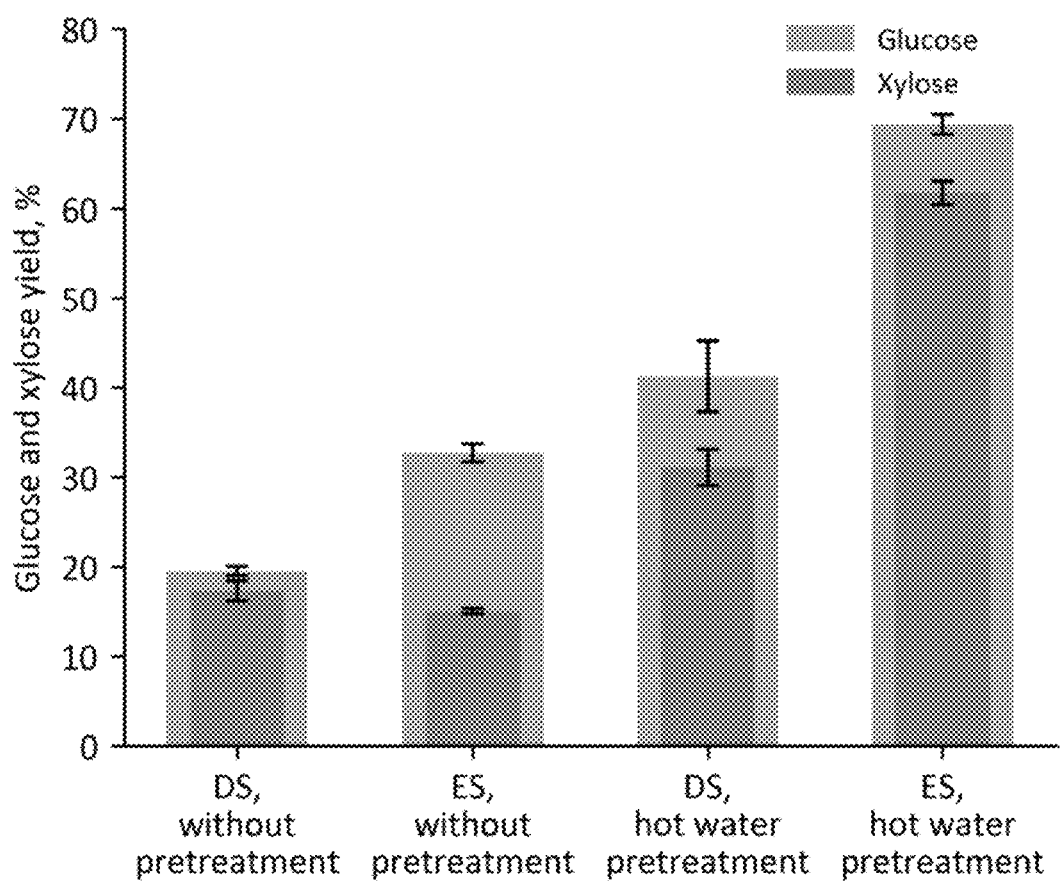
FIG. 1B. Comparison of the compositions of dry sorghum and ensiled sorghum.
FIG. 2. Glucose and xylose yields from raw (without pretreatment) and hot water pretreated biomass sorghum after 72 h of enzymatic hydrolysis.

Biomass compositional analysis is required to understand the quality and nature of feedstocks for any biomass conversion processes. The compositional analysis of dry sorghum (DS) and ensiled sorghum (ES) indicate considerable differences between the feedstocks. The ES contained high moisture in the range of 65 to 75%, while the moisture content of the field DS is approximately 20%. The anaerobic fermentation during the ensiling process (wet storage) generates weak organic acids, which bring down the ensiled biomass pH to a value close to 4. On the other hand, the pH of the DS stays around 7. FIGS. 1A and 1B summarize the detailed composition analysis of both ES and DS feedstocks.

One of the key differences between both feedstocks is the extractive content (FIG. 1i). The DS contained around 18% of extractives, which are primarily monosaccharides such as glucose, fructose and smaller amounts of xylose, galactose, and arabinose. In contrast, the extractive content in the ES material reached 26%, mainly due to higher amounts of lactic (8-9%) and acetic (3-4%) acids, despite having a relatively lower mono- and polysaccharide content (FIG. 1A). These results are not surprising because the microorganisms that are present during the ensiling process ferment the sugars into organic acids. The compositional analysis results also show that there is a small reduction in the amount of structural carbohydrates such as cellulose and hemicellulose in the ES, likely due to their partial fermentation.

3.2. One-Pot IL Pretreatment of Dry and Ensiled Biomass Sorghum

A control saccharification of both DS and ES is carried out to determine the relative enhancement elicited by the one-pot biomass deconstruction process considered in this study. As expected, DS in the absence of pretreatment produced very low yields of glucose (19%) and xylose (17%) after enzymatic hydrolysis (FIG. 2 and Table 1). However, the use of ES showed a positive effect by increasing the glucose yields to 32%, in agreement with previous reports. The benefit of using ensiled material is also observed when a hot water pretreatment (without any IL) is included, which increased the yields of glucose (69%) and xylose (60%) in ES relative to the DS (FIG. 2 and Table 1). With this in mind, the effects of using the ES in a one-pot IL process configuration for lignocellulosic sugar conversion to a biofuel precursor molecule are investigated. The four main economic criteria used in this comparison are the ionic liquid loading concentration, requirements for pH adjustment after pretreatment, enzyme loading rate, and hydrolysis time.

3.2.1. Effect of Ionic Liquid Loading

Figure 3:
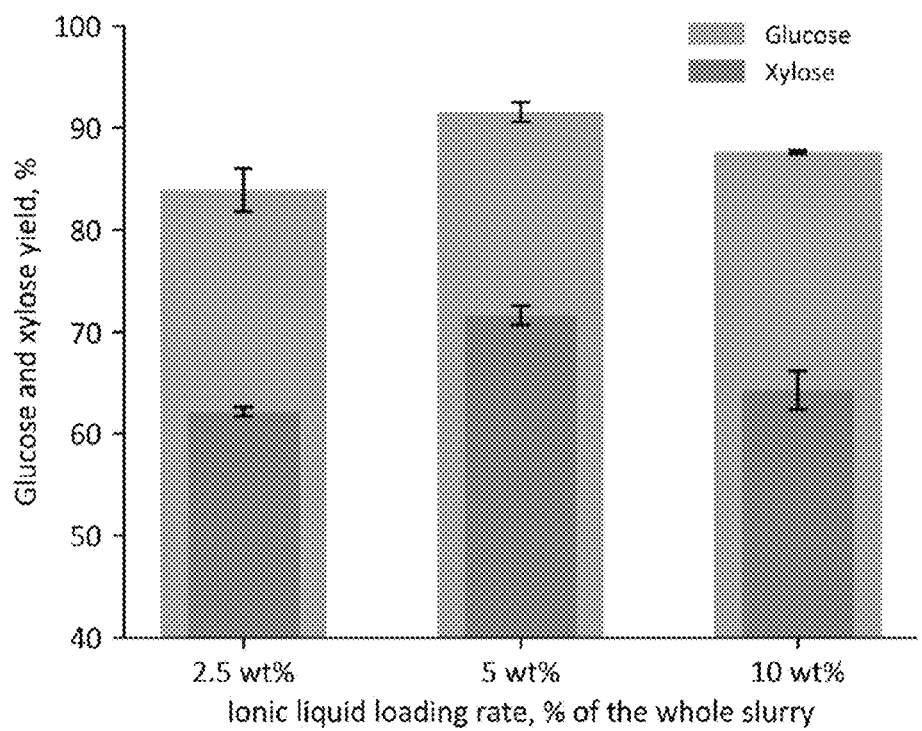
FIG. 3. Glucose and xylose yields obtained by performing a one-pot IL process utilizing the ES. The IL loading rates are 2.5, 5, and 10 wt % based on the whole slurry.

The biomass deconstruction efficiency of three different concentrations of the IL [Ch][Lys] (2.5, 5, and 10 wt %) is determined from both DS and ES in a one-pot process configuration. The results show that the presence of IL and subsequent enzymatic saccharification resulted in a higher total monomeric sugar yield in all cases, when compared to the hydrothermal pretreatment (FIG. 3 and Table 1). The highest glucose yield of 92% is observed with ensiled biomass at an IL concentration of 5%.

Figure 10:
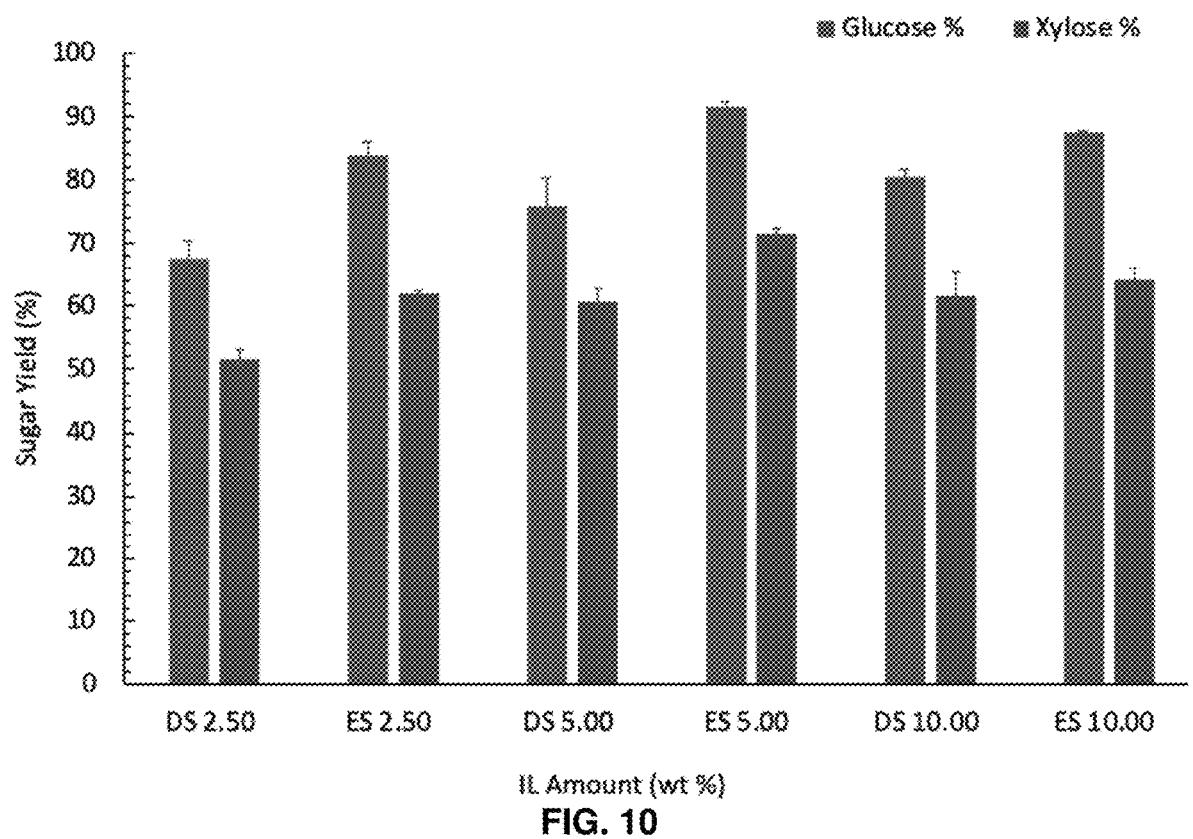
FIG. 10. Glucose and xylose yields obtained by performing a one-pot IL process utilizing the ensiled and dry biomass sorghum. The IL loading rates are 2.5, 5, and 10 wt % based on the whole slurry.
Figure 11:
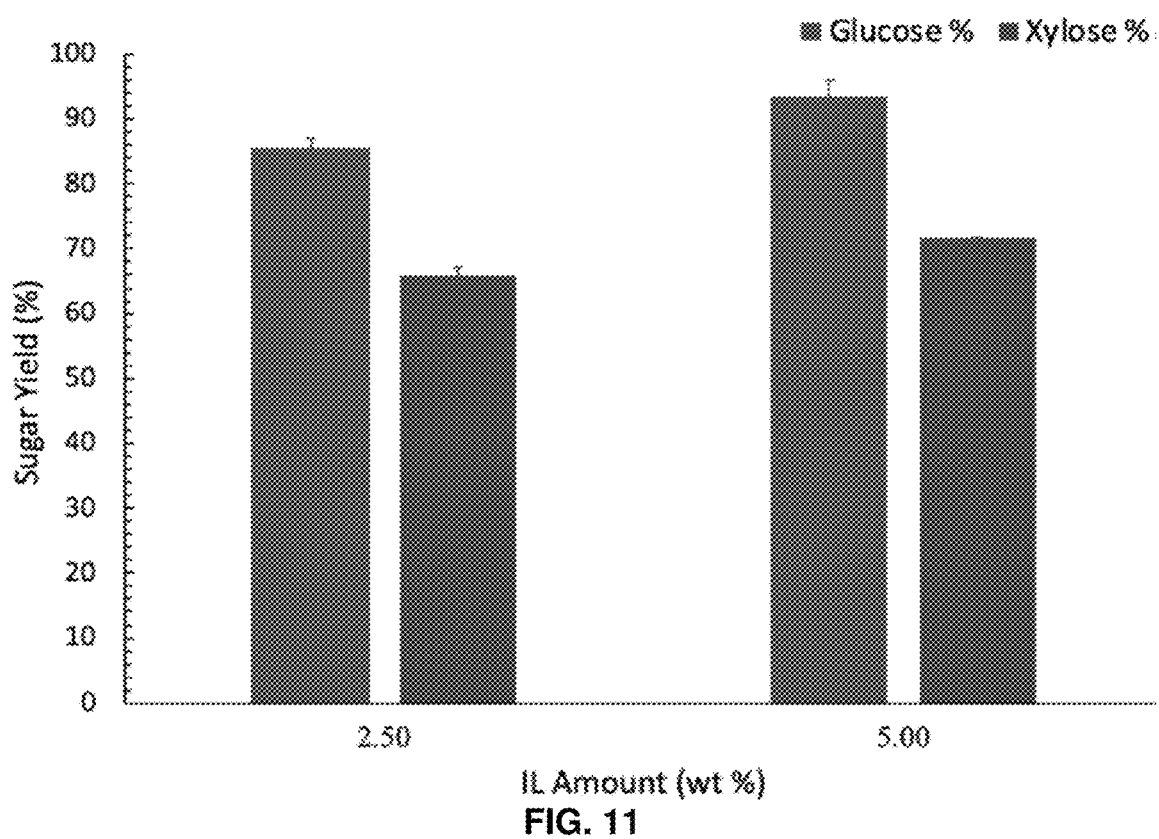
FIG. 11. Glucose and xylose yields obtained by performing a one-pot IL process utilizing the ES in Parr reactor at 140° C. The IL loading rates are 2.5 and 5 wt % based on the whole slurry.
Figure 12:
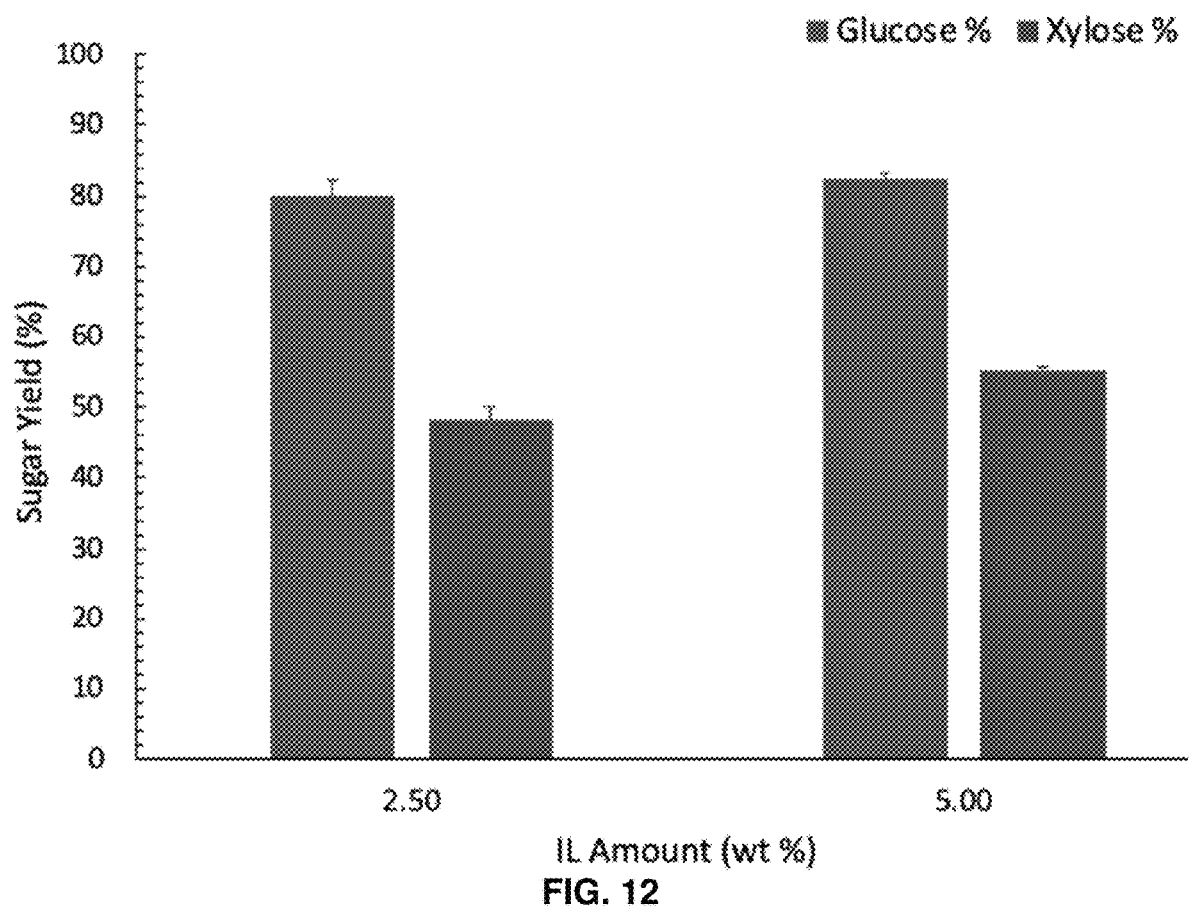
FIG. 12. Glucose and xylose yields obtained by performing a one-pot IL process of ES at 95° C. The IL loading rates are 2.5 and 5 wt % based on the whole slurry.
Figure 13:
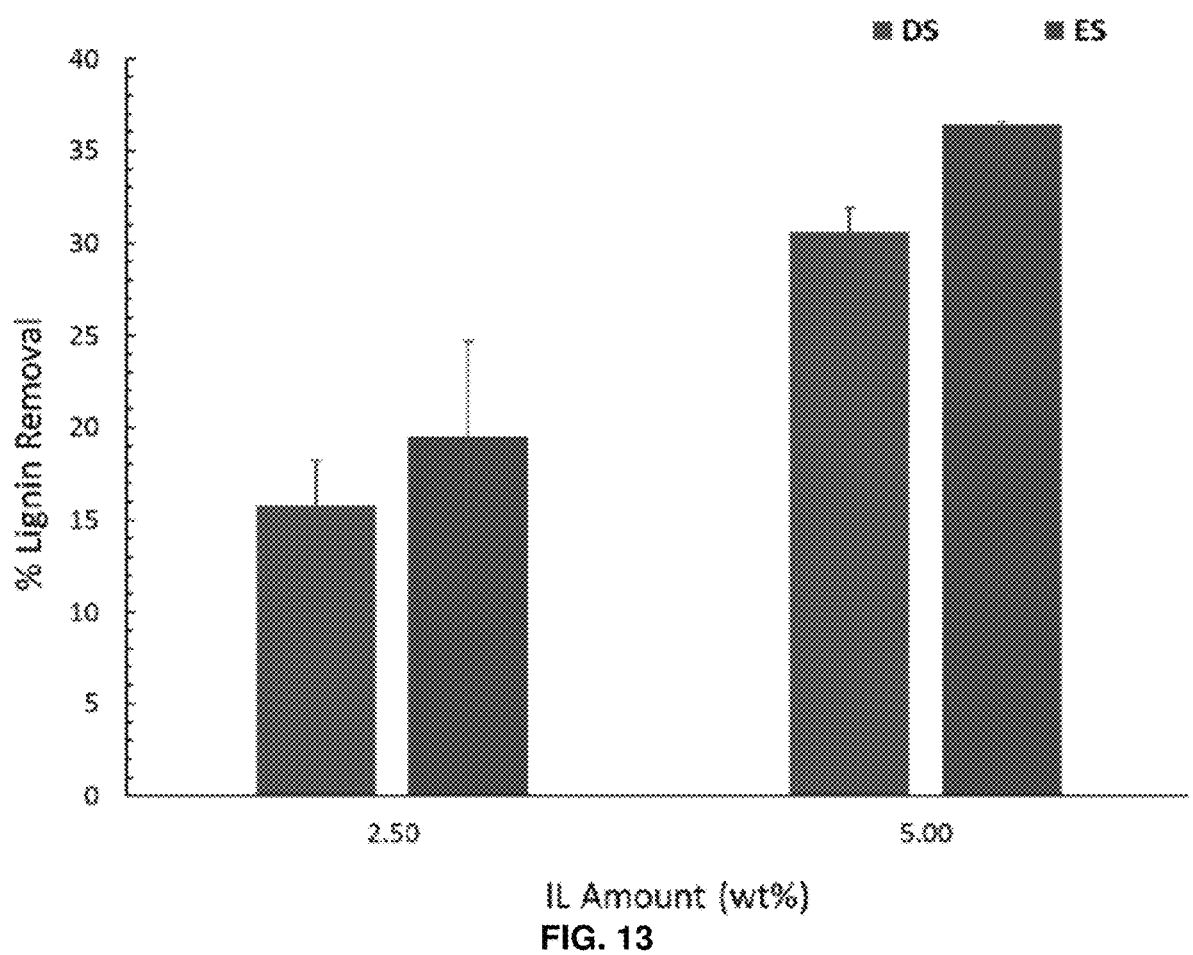
FIG. 13. Lignin removal of ES and DS biomass during the IL pretreatment. The IL loading rates are 2.5, and 5 wt % based on the whole slurry.

These results show that the ES pretreatment resulted in ~10-15% more glucose when compared to the respective DS pretreatment (Table 1 and FIG. 10) Interestingly, the xylose yield is not significantly improved relative to glucose and remained below 75% of the maximum. This may be due to the presence of organic acids in ES and it may have a negative effect on the enzymes during the enzymatic hydrolysis step.

TABLE 1

Comparison of glucose and xylose yields obtained by performing enzymatic saccharification to dry or ensiled sorghum pretreated with IL, hot water, or not pretreated.

| | Dry sorghum (DS) | | Ensiled sorghum (ES) | |
|---|---|---|---|---|
| Pretreatment | % Glucose | % Xylose | % Glucose | % Xylose |
| None | 19.54 (±0.54) | 17.30 (±1.12) | 32.71 (±1.10) | 15.08 (±0.29) |
| Hot Water | 41.22 (±3.96) | 31.07 (±2.01) | 69.38 (±1.11) | 61.75 (±1.33) |
| [Ch][Lys] 2.5% | 67.51 (±2.84) | 51.78 (±1.35) | 83.90 (±2.10) | 62.11 (±0.45) |
| [Ch][Lys] 5% | 75.86 (±4.45) | 60.76 (±2.06) | 91.54 (±0.98) | 71.64 (±0.96) |
| [Ch][Lys] 10% | 80.52 (±0.16) | 61.68 (±3.63) | 87.62 (±0.16) | 64.26 (±1.92) |

To study the scalability of the pretreatment process, the optimized pretreatment conditions of ES is applied to a scaled-up process using a benchtop 1 L Parr reactor. Enzymatic saccharification of the pretreated ES at 140° C., released >93% and >85% of the maximum theoretical glucose at the IL-loadings of 5% and 2.5%, respectively. Also, the glucose and xylose yields are reported around ~82% and ~55% (see FIGS. 10-13) when the pretreatment temperature is decreased from 140 to 95° C. Interestingly this shows a greater potential to eliminate the pressure reactors for ES one pot pretreatment to achieve higher sugar conversions.

3.2.2. pH Adjustment after Pretreatment

Figure 4:
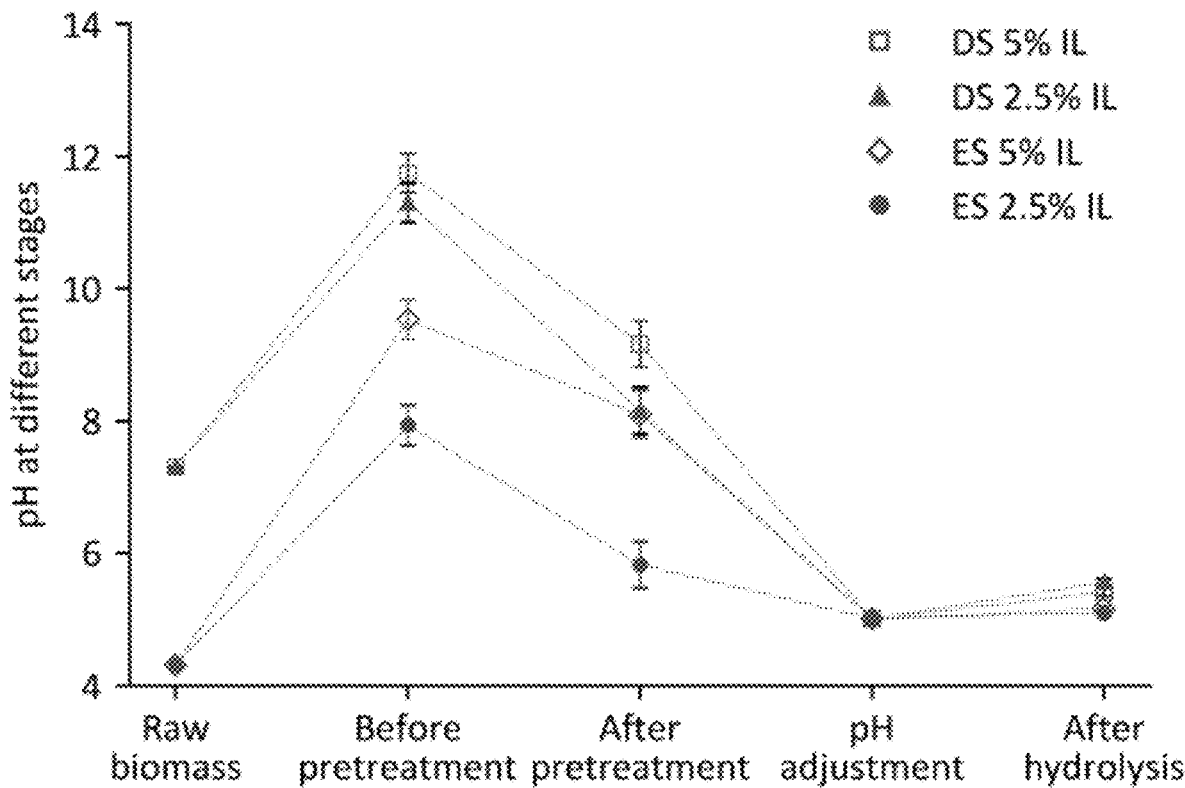
FIG. 4. pH variations at several stages of the biomass deconstruction process.

It is observed that pretreatment of the ES with [Ch][Lys] results in a significant pH difference relative to the DS, which is not unexpected as ES has a lower initial pH than DS. The untreated ES has a pH of 4.3, which is more acidic compared to the DS with a pH of 7.3. [Ch][Lys] is a basic IL with a pH of around 12. Upon addition of the 2.5 wt % of the IL, the starting pH of the ES increased from pH 4.3 to pH 7.85. A similar trend is observed in DS as well and its pH increased to pH 11 from starting pH of 7.3 (FIG. 4). Usually after the pretreatment, the pH of the biomass slurry decreased relative to the initial pH. This is possibly due to the formation of acidic moieties such as acetic acids from the processes such as deacetylation of hemicellulose at higher pretreatment temperatures.[31,32] After the pretreatment, the pH of the DS slurry slightly decreased to pH of 9.5 from 11, while the pH of the ES slurry is decreased from 7.85 to 5.65. The optimum activity of the enzymes used for saccharification is in the range of pH 4.8-5.5. Therefore, after the [Ch][Lys] IL pretreatment, the pretreated DS slurry requires a pH adjustment prior to the enzymatic hydrolysis, while the 2.5 wt % [Ch][Lys] IL pretreated ES does not. This is a major advantage of the ensiled biomass feedstock, which helps to reduce capital and operating costs required for the pH adjustment when this system is commercially deployed.

3.2.3. Enzyme Loading Rate

Optimization of the fully consolidated IL pretreatment and enzymatic saccharification processes is an important step before commercial deployment. The amount of the enzymes used for saccharification can significantly alter the overall biofuel production cost and greenhouse gas emissions. In order to achieve an economically viable biofuel production technology, the enzyme loading must be reduced while maintaining a high saccharification efficiency. Several past studies used enzyme loading rate typically in the range of 20-30 mg of protein per g of glucan to achieve higher glucose and xylose yields.[25,33,34] Here the enzymatic hydrolysis of DS and ES are carried out using the commercial enzyme cocktails, Novozymes Cellic® CTec3 and HTec3. In this work, the effect of enzyme loading on glucose and xylose yields during saccharification process considering the pretreated ES at three different ([Ch][Lys]) IL loading rates of 2.5, 5, and 10 wt % and pretreatment temperature and time of 140° C. and 3 h, respectively is demonstrated. For each enzymatic hydrolysis process, the enzyme loadings are normalized based on the resulting glucan and xylan contents of the pretreated biomass, which are determined using the standard composition analysis methods.[23] The saccharification process is carried out at 50° C. for 72 h.

Figure 5:
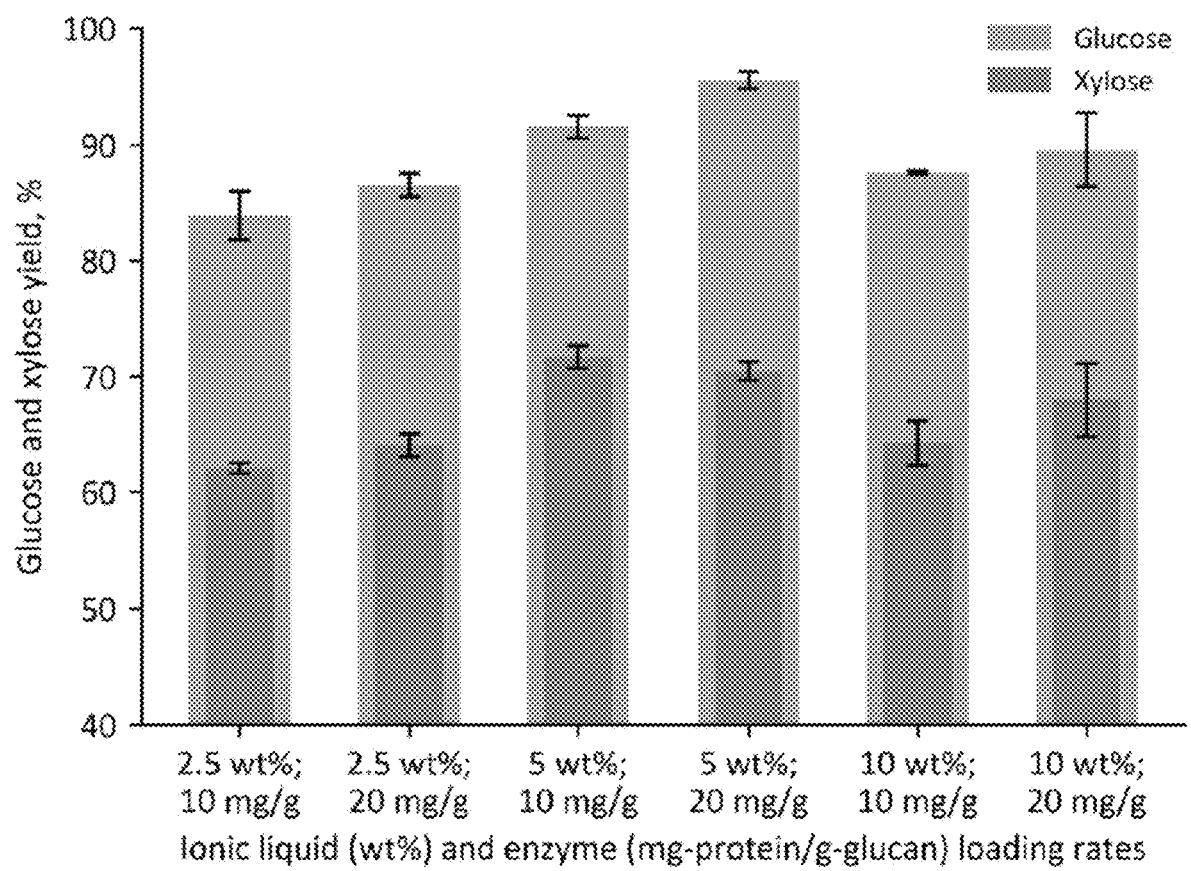
FIG. 5. Glucose and xylose conversions after enzymatic hydrolysis of the pretreated ES at different enzyme loadings.

Even though the enzyme loading decreased from 20 to 10 mg $g^{-1}$ of starting biomass, the sugar conversions remained the same as the higher loadings during the enzymatic hydrolysis. Glucose yields shows slight decrease from 86.5 g/L to 83.9 g/L, 95.5 g/L to 91.5 g/L and 89.5 g/L to 87.6 g/L for the ES pretreated at the IL loadings of 2.5, 5, and 10 wt %, respectively. (FIG. 5). Also, a similar behavior observed for xylose conversion. These observations highlight the importance of the ensiled biomass feedstock for reducing the enzyme loadings and achieving a higher sugar conversion relative to DS.

3.2.4. Enzymatic Hydrolysis Time

Figure 6:
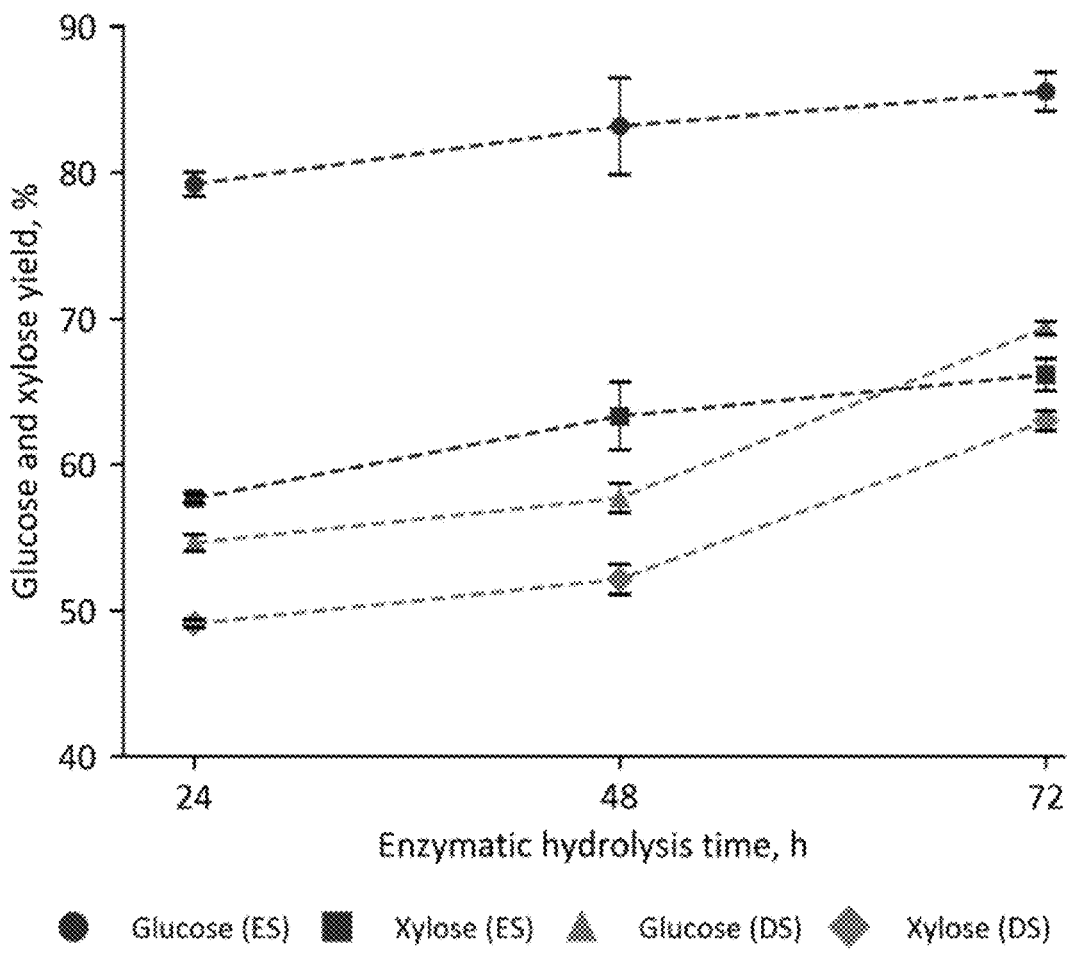
FIG. 6. Glucose and xylose yields during different time intervals of enzymatic hydrolysis of the 2.5 wt % [Ch][Lys] IL pretreated ES and DS at 50° C.

As discussed earlier, using a lower enzyme loading and achieving a high sugar conversion in one-pot process is a key factor for reducing the biofuel production cost and greenhouse gas emissions. At the same time, reducing the enzymatic hydrolysis time decreases the reactor size or quantity and energy consumption. Current enzymatic hydrolysis process for DS requires 48 to 72 h to reach the maximum sugar conversion. Here the enzymatic hydrolysis efficiency for 2.5 wt % of the IL pretreated ES and DS is monitored and sugar conversions are analyzed at 24 h, 48 h and 72 h time intervals. Results show that the ES requires a short hydrolysis time in between 24-48 h to release most of the sugars relative to DS (FIG. 6).

3.3. Fermentations on Hydrolysates Generated Using the One-Pot ES Process

One crucial parameter for the valorization of lignocellulosic biomass is the compatibility of the generated hydrolysates with microbial conversion of the depolymerized sugars, organic acids and aromatics. Parameters like the type of feedstock, chemicals and conditions used for pretreatment, final pH, and the concentration of inhibitory compounds in the final hydrolysates have a strong influence on the performance of the fermenting organism. With this in mind, evaluations are made as to if the hydrolysates generated under the conditions that promoted the highest sugar release can be used to cultivate *R. toruloides*. This oleaginous red yeast is chosen as a conversion host because it has been previously demonstrated to be tolerant to salts, relatively low pH conditions, and compounds commonly generated during the thermochemical and enzymatic depolymerization of lignocellulosic biomass. The fact that this organism does not require any vitamins, antibiotics, inducers or amino acid supplements for growth and product formation also contributes to lower the fermentation costs. In addition, *R. toruloides* is known to be able to co-utilize glucose, xylose, and some aromatic monomers to generate cell biomass rich in lipids and carotenoids, and can be engineered to accumulate non-native bioproducts like terpenoids or peptide-based pigments. Because of this naturally advantageous metabolism, an engineered strain with the ability to produce bisabolene called GB2.0 is previously obtained in our laboratory. Here performance of this strain is evaluated as the biofuel producer in a ES one-pot IL process that includes a fermentation step. Cultivations are set using hydrolysates supplemented only with ammonium sulfate as nitrogen source, and the final cell biomass, substrate consumption and bisabolene production are measured after 5 days of incubation. The toxicity of the media is evaluated by comparing two hydrolysate concentrations, 90% and 50% of the original hydrolysates, after diluting with water. The results of these experiments are shown in Table 2.

*R. toruloides* GB2.0 displays robust growth and bisabolene production in the four tested conditions. Complementary to the data presented in FIG. 4, Table 2 shows that both IL concentrations released similar amounts of glucose, xylose, acetic and benzoic acids, and these compounds are almost completely consumed in all cases. Although the final cell biomass did not change significantly when using different IL loadings or hydrolysate concentrations, the bisabolene titers changed proportionally to the amount of substrate present in the diluted hydrolysates before inoculation. These results support the use of pretreated and saccharified ensiled sorghum in a one-pot configuration for biological conversion using a low IL concentration of 2.5%. The engineered strain did not display any apparent inhibition in growth or production capabilities caused by the more concentrated media, suggesting that it can be possible to implement higher pretreatment solid loadings and avoid hydrolysate dilutions to increase product titers.

TABLE 2

Bisabolene titers, final cell biomass and substrate utilization values obtained after cultivation of engineered *R. toruloides* in hydrolysates generated using the ES IL one-pot process.

| IL loading (%) | Hydrolysate concentration (%) | Bisabolene titer (mg/L) | Final cell biomass (OD$_{600}$) | Initial substrate concentration (g/L) Substrate Utilization (%) | | | |
|---|---|---|---|---|---|---|---|
| | | | | Glucose | Xylose | Acetic | Benzoic |
| 2.5 | 90 | 1178 ± 189 | 13.6 ± 0.2 | 46.7 | 17.6 | 4.3 | 0.5 |
| | | | | 98.6 ± 0.2 | 94.0 ± 1.5 | 100.0 ± 0.0 | 94.9 ± 0.8 |
| 5 | | 1385 ± 266 | 13.0 ± 0.2 | 53.9 | 20.8 | 4.6 | 0.6 |
| | | | | 97.4 ± 0.2 | 92.5 ± 0.4 | 100.0 ± 0.0 | 99.0 ± 0.8 |
| 2.5 | 50 | 583 ± 81 | 12.3 ± 0.2 | 26.1 | 9.8 | 2.3 | 0.3 |
| | | | | 98.8 ± 0.1 | 97.9 ± 0.3 | 100.0 ± 0.0 | 83.0 ± 6.2 |
| 5 | | 627 ± 53 | 11.8 ± 0.4 | 27.0 | 10.6 | 2.2 | 0.3 |
| | | | | 97.4 ± 0.1 | 95.4 ± 0.3 | 100.0 ± 0.0 | 90.9 ± 8.0 |

3.4. Minimum Selling Price and Carbon Footprint of Biofuels

Figure 7:
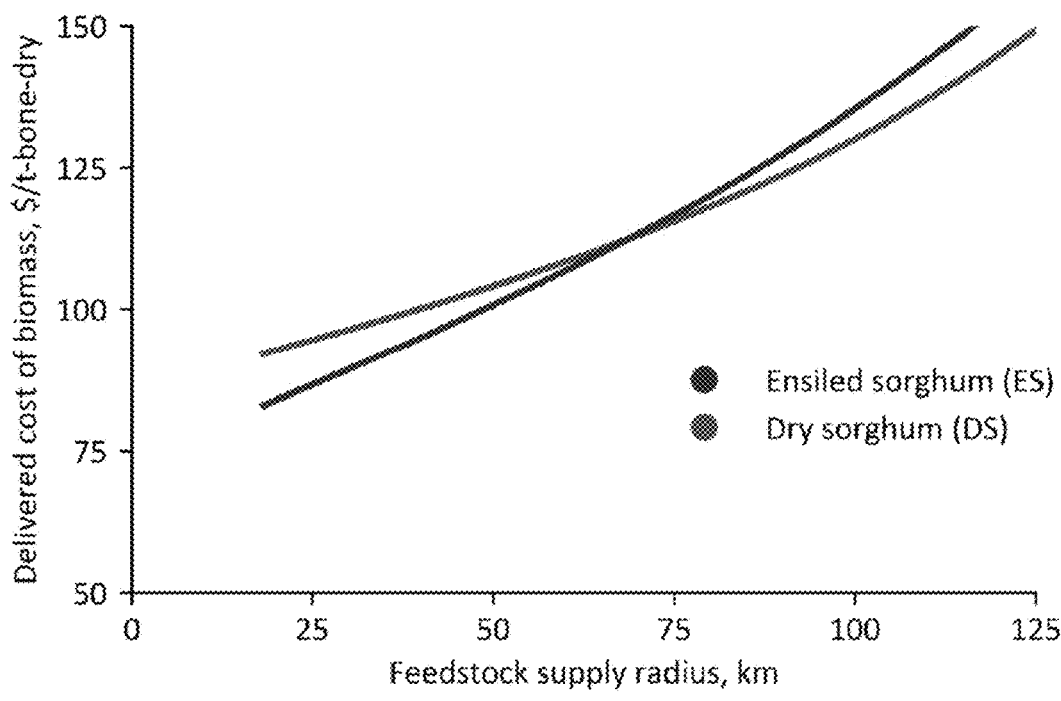
FIG. 7. DS and ES feedstocks supply costs. The dry feedstock is delivered in the form of bale (20% moisture) and stored next to the biorefinery under the tarp. The ES supply chain includes the direct transportation of chopped biomass (60% moisture) from the field to the biorefinery and ensiled next to the biorefinery in the bunker silo and covered with a tarp. The overall supply cost is presented per bone-dry metric ton (t) of dry or ES feedstock.

FIG. 6 shows the delivered cost of dry and ensiled biomass sorghum as a function of distance from the field to the biorefinery. This includes the cost associated with biomass production, harvesting, transportation, and storage. Despite dry down from the moisture content at the time of harvest of 60 to 20% in the field, it is found that the ensiled chopped-biomass sorghum supply system is economically feasible for the feedstock supply radius of <65 km (<40 miles) when compared to the dry biomass sorghum supply system in the form of bale (FIG. 7). This is mainly due to additional costs associated with the biomass bale including field drying, baling, and stacking. Additionally, the field drying process is highly uncertain and dependent on the local climate. Therefore, the location of the biorefinery and ease of the downstream conversion process determine the selection of an appropriate form of biomass feedstock. This study considers the economic cut-off supply radius of 65 km (40 miles) to determine process economics and carbon footprint of the cellulosic biorefinery utilizing the dry and ensiled biomass sorghum feedstocks.

Figure 8:
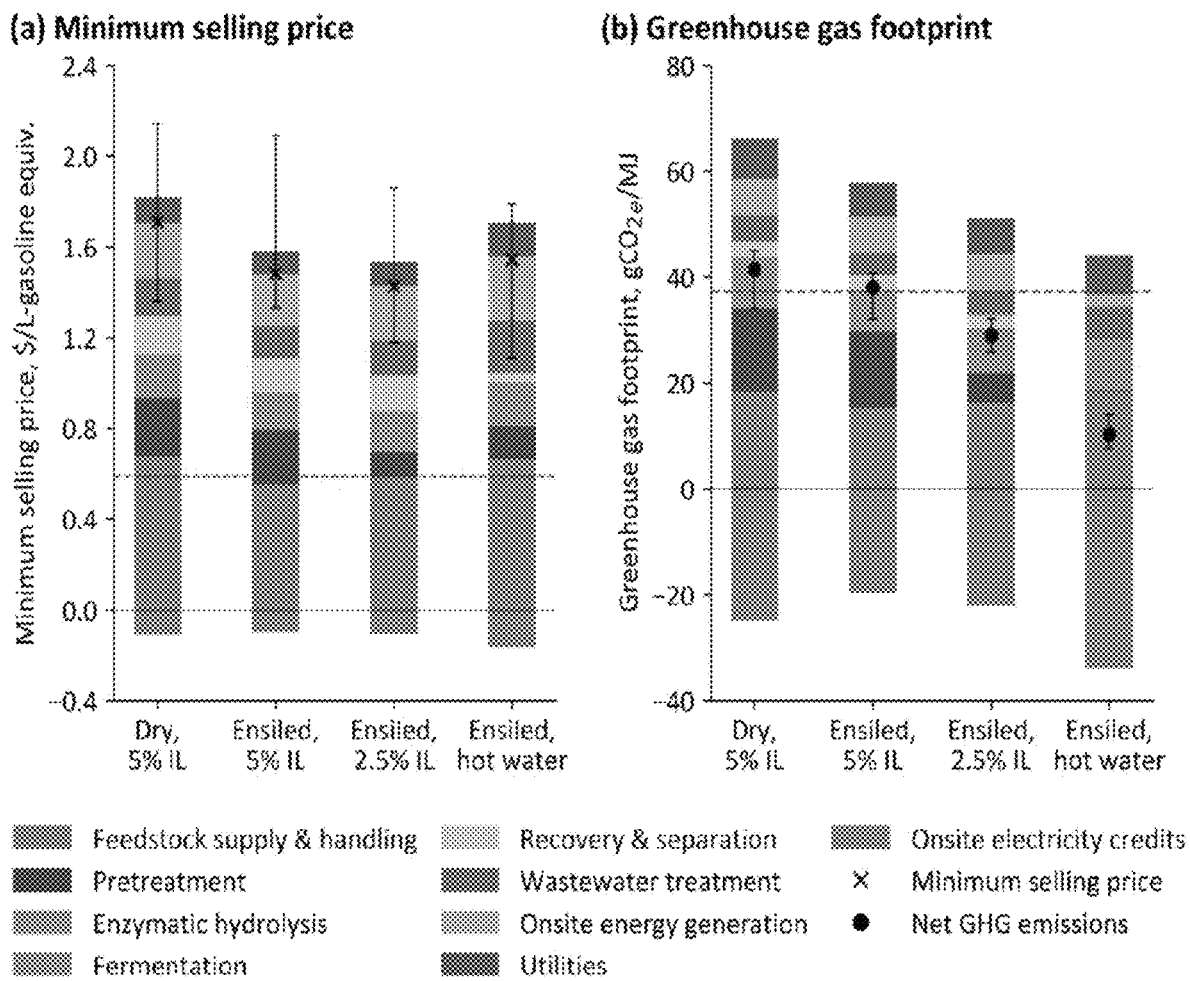
FIG. 8. Minimum selling price and greenhouse gas footprint of ethanol utilizing dry and ensiled biomass sorghum feedstocks. The sensitivity bars represent the pessimistic and optimistic results considering the sugar yield of 50% and 90% of the theoretical yield, respectively. The horizontal dashed lines represent (a) last 10-year (2009-2018) average gasoline selling price at the refinery gate of $0.59/L; and (b) the Renewable Fuel Standard (RFS) GHG emissions reduction target of 37.2 gCO2e/MJ (60% reduction relative to the petroleum baseline).[27]

Utilization of the ES feedstock reduces the minimum selling price of ethanol by 13.4% relative to the DS at the IL-loading rate of 5 wt % (based on the whole slurry). This reduction is mainly due to an increased yield of both glucose and xylose (FIG. 3) relative to the DS feedstock. The process if found to be more economical utilizing the ES a low IL loading rate of 2.5 wt %, which reduces the minimum selling price of ethanol by 16.7% relative to the DS at the IL loading rate of 5 wt % and by 7.6% relative to the liquid hot water pretreatment of the same ES feedstock (FIG. 8). This large reduction in selling price is due to a lower material cost for biomass pretreatment and very competitive sugar yield (FIG. 3). The variations in sugar yield at the same pretreatment condition largely impact on the minimum selling price, which is represented by the sensitivity bars (FIG. 8).

Cost, availability, and the quality of biomass feedstock are always important for the success of future cellulosic biorefineries as biomass feedstock supply accounts for 40% of the total ethanol production cost. Biomass deconstruction, including pretreatment and hydrolysis, is another essential unit operation and is responsible for 23% of the total ethanol production cost. This cost contribution can reduce to 15% by utilizing the ensiled biomass sorghum feedstock at a low IL loading rate of 2.5 wt %. However, supplying the chopped/ ensiled biomass sorghum for a large scale biorefinery located away from the field (>65 km) can be a challenge. This issue can be resolved by building the sugar production depots close to the field and transporting the concentrated sugar from the sugar depots to the biorefineries located away from the field. This allows utilization of the ensiled biomass feedstock regardless of the locations of biorefineries which not only helps for the economic and efficient biomass deconstruction but also lowers the overall feedstock supply cost.

Similar to the ethanol production cost, utilizing the ensiled biomass sorghum feedstock at the biorefinery minimizes the overall GHG by 8.2% and 29.8%, respectively, at the IL loading rates of 5 wt % and 2.5 wt % relative to the dry biomass sorghum feedstock at the IL loading rate of 5 wt %. This is mainly due to improved biomass deconstruction efficiency (FIG. 3), reduced makeup IL, and minimized neutralizing chemicals, such as sulfuric acid (FIG. 4). While the liquid hot water pretreatment is not economical relative to the IL pretreatment at the IL loading rate of 2.5 wt %, it reduces the overall GHG emissions by 64.6%. This large reduction in GHG emissions is due to the absence of ionic liquid and a large carbon credit from the onsite electricity. A low biomass deconstruction efficiency of the hot water pretreatment results in a large fraction of the unutilized cellulose, hemicellulose, and lignin, which are primarily responsible for generating onsite electricity. However, GHG emissions credit from the electricity beyond the facility use (48% of the total electricity credits) is very uncertain and dependent on its utilization for other purposes including selling to the National Grid.

It is found that IL-based biomass deconstruction process at 5 wt % IL loading rate accounts for 51% of the net GHG emissions and reduced to 36% at the IL loading rate of 2.5 wt %. In addition to IL, enzyme, and sulfuric acid (used for pH adjustment) are other sources of GHG emissions for the biomass deconstruction process. Future process improvements including hydrolysis at low enzyme loading rate and elimination of the required neutralizing chemical will further reduce the carbon footprint of the biorefinery.

Unsurprisingly, the first demonstrated bisabolene production in a one-pot process by using *R. toruloides* (Table 2) results in a very large minimum selling price of bisabolane (jet fuel equivalent hydrogenated product) in the range of $25.7-31.5/L-Jet A. However, the selling price can reach to $0.8/L with further process optimizations.[24] Some of the identified process improvement opportunities in our previous study,[24] such as a low IL and enzyme loading rates, are achieved in this study. In addition to biofuel, lipid content in *R. toruloides* (up to 60 wt %.) can be recovered and transformed into value-added bioproducts/biofuels.[35] This potential opportunity should be explored in future to fully quantify the bisabolene production cost and associated GHG emissions using *R. toruloides*.

3.5. Cost and Carbon Footprint Drivers Associated with Biomass Deconstruction

Figure 9:
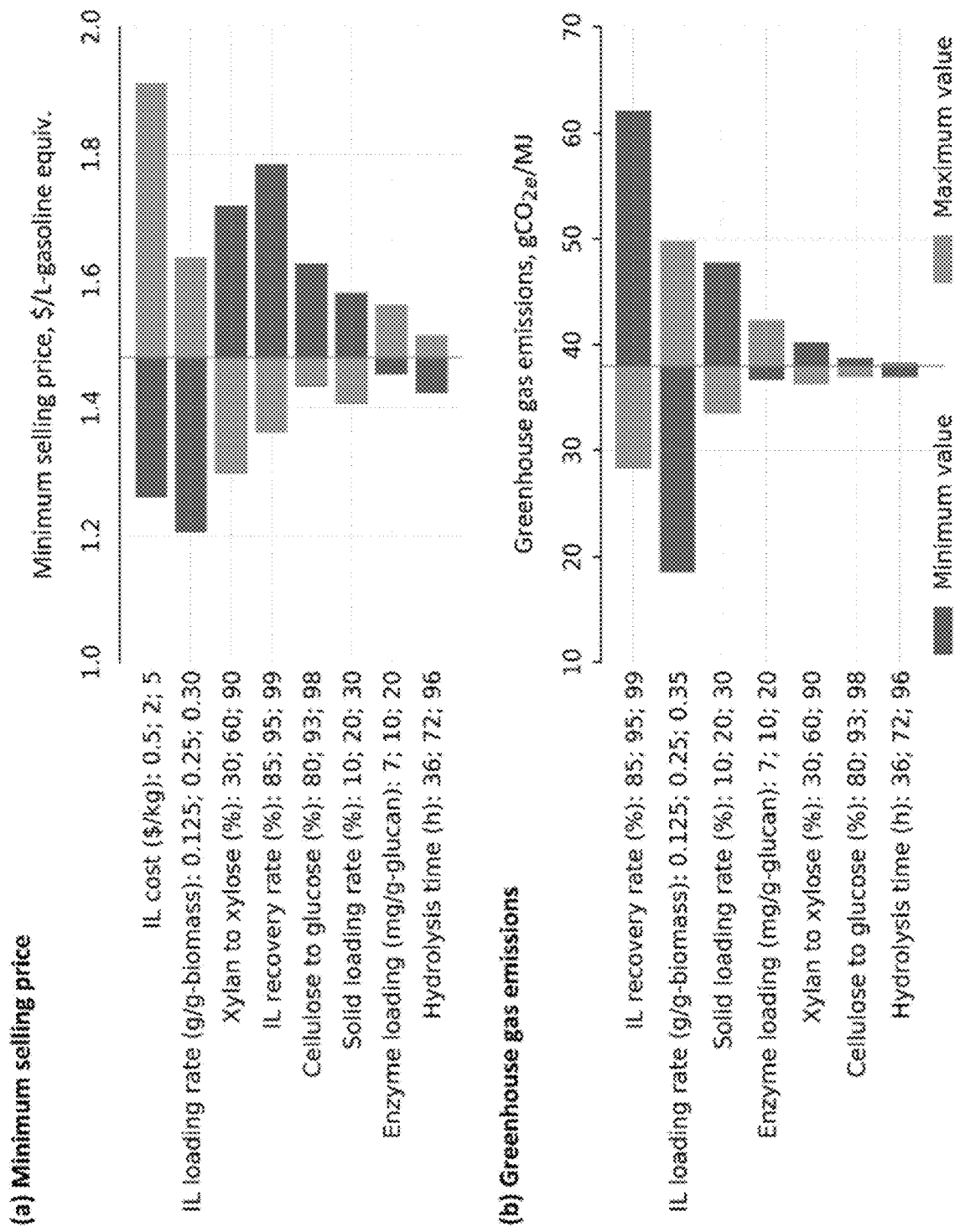
FIG. 9. Most influential input parameters associated with biomass deconstruction. This is a representative case considering the ensiled biomass sorghum at the IL loading rate of 5 wt %.

FIG. 9 depicts the main cost and carbon footprint drivers associated with biomass deconstruction process. IL cost is obviously influential to the minimum selling price of ethanol. This warrants a continuous research on identifying a cheap IL for lignocellulosic biomass deconstruction. Additionally, changes in IL loading and recovery rates alter the amount of makeup IL; therefore, both are influential to the selling price and GHG emissions of ethanol. Utilization of the ensiled biomass feedstock can be a stepping stone for a sustainable operation of cellulosic biorefineries in the future as it requires a low IL loading rate for effective biomass deconstruction. Future research efforts are required to achieve the targeted IL recovery rate of 99% with a minimal expenditure of cost and energy. Other influential parameters include glucose and xylose yields, solid and enzyme loading rates, and hydrolysis time. While the sugar yield directly alters the amount of biofuels, other parameters alter either the required amount of material (such as enzymes) or utilities and the size of process equipment thereby influential to both cost and GHG emissions of ethanol.

The synergistic impacts of the most influential input parameters, including IL loading rate of 2.5 wt %, IL recovery of 99%, sugar yield of 90% of the theoretical yield, solid loading rate of 30 wt %, enzyme loading rate of 7 mg of protein per g of glucan and hydrolysis time of 36 h reduces the overall ethanol selling price and GHG emissions to $1.1/L-gasoline-equivalent and 21.4 gCO2e/MJ, respectively. Future research can focus on achieving these targets although systemwide improvements are required to achieve the market-competitive price of ethanol (FIG. 9).

4. Conclusions

Figure 14:
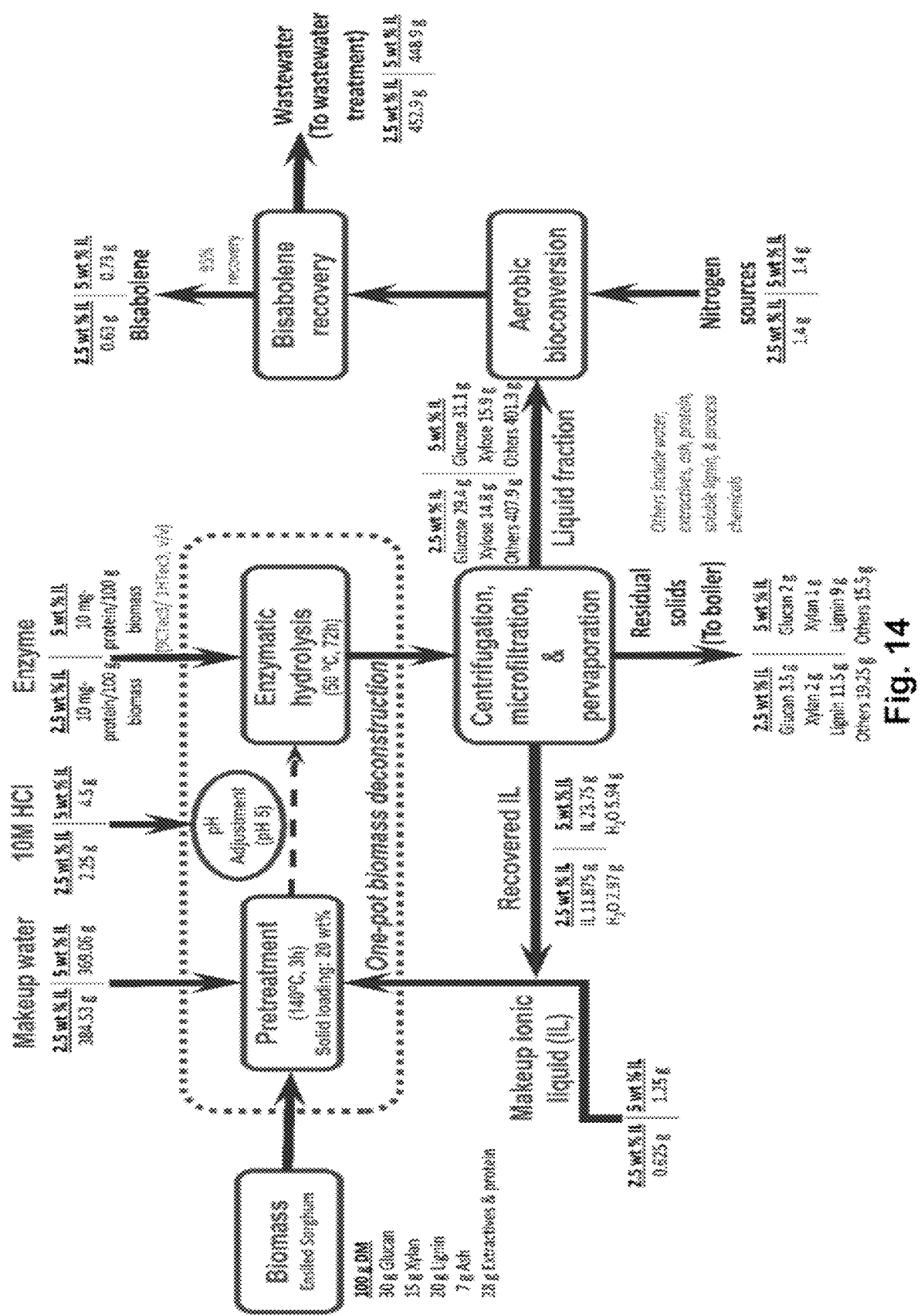
FIG. 14. Process configuration and mass balance analysis considering bisabolene as a representative biofuel and ionic liquid and bisabolene recovery rates of 95%. Bisabolene production in *R. toruloides* using the whole biomass hydrolysate currently results in a low yield of bisabolene. The process demonstrated herein requires further process optimization to improve titer, rate, and yield of bisabolene. In the current biorefinery model, the residual solid (mainly lignin) is routed to the boiler to generate process heat and electricity. However, if the lignin fraction of biomass could be upgraded into value-added products, the selling price and carbon footprint of bisabolane could be further reduced.

Ensiled biomass sorghum is found to be an effective feedstock for the IL-based biorefineries. This enables a considerable decrease in the amount of ionic liquid usage, mild pretreatment conditions, and a higher sugar yield relative to the unensiled biomass, thereby reducing the production cost of biofuel and associated carbon footprint. The biomass deconstruction and bioconversion processes considered in this study eliminate the requirement for IL separation prior to enzymatic hydrolysis and bioconversion processes. Additionally, the selected technology fundamentally allows the one-pot process due to enzyme- and biocompatible ionic liquid, which has a great potential to reduce the overall cost and the environmental footprint of the biorefinery. As much as 16.7% reduction in ethanol production cost and 28.9% reduction carbon footprint with the improved process utilizing ensiled biomass at the IL loading rate of 2.5 wt % relative to the conventional system utilizing the unensiled biomass sorghum at the IL-loading rate of 5 wt % is found. The process can be implemented in other biofuels/bioproducts production pathways that can help to establish sustainable cellulosic biorefineries in the future. FIG. 14 summarizes experimental data and process configuration considering bisabolene as a representative case.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method to deconstruct a biomass: the method comprising:
   (a) ensiling a biomass to produce one or more organic acids,
   (b) introducing a solvent to the ensiled biomass to dissolve at least part of solid biomass in the solvent, wherein the solvent is an ionic liquid (IL), to form a solubilized biomass mixture, wherein the solvent introduced is 2.5 to 10% by weight of the ensiled biomass,
   (c) introducing an enzyme to the solubilized biomass mixture such that the enzyme produces a sugar from the solubilized biomass mixture, and
   (d) introducing a genetically modified host cell to the solubilized biomass such that the genetically modified host cell converts the sugar produced from the biomass into a biofuel or chemical compound.

2. The method of claim 1, wherein the enzyme is a cellulase.

3. The method of claim 1, wherein the method further comprises (e) separating the sugar from the solubilized biomass mixture.

4. The method of claim 1, wherein steps (a), (b), (c) and (d) do not comprise or lack introducing or adding any water to the biomass or biomass mixture.

5. The method of claim 1, wherein an amount of sugar produced in step (c) is equal to or more than an amount of sugar produced using an identical method except the identical method lacks the ensiling step (a) and the identical method using equal to or more than double an amount of the IL used in step (b).

6. The method of claim 2, wherein the genetically modified host cell is resistant to the one or more organic acids.

7. The method of claim 6, wherein the organic acid is acetic acid, lactic acid, formic acid, or an aromatic organic acid.

8. The method of claim 7, wherein the organic acid is benzoic acid or vanillic acid.

9. The method of claim 1, wherein the IL comprises an organic ammonium-based cation and an organic carboxylic acid-based anion.

10. The method of claim 1, wherein the IL comprises a quaternary ammonium salt with an amine, amide, alcohol, or carboxylic acid.

11. The method of claim 1, wherein the genetically modified host cell is *Rhodosporidium toruloides*.

* * * * *